(12) United States Patent
Gorodetsky et al.

(10) Patent No.: US 7,122,620 B1
(45) Date of Patent: Oct. 17, 2006

(54) HAPTOTACTIC PEPTIDES

(75) Inventors: Raphael Gorodetsky, Jerusalem (IL); Gerard Marx, N.Y., NY (US)

(73) Assignee: Medical Research Services and Development Ltd., Jerusalem (IL)

( * ) Notice: Subject to any disclaimer, the term of this patent is extended or adjusted under 35 U.S.C. 154(b) by 0 days.

(21) Appl. No.: 09/487,790

(22) Filed: Jan. 20, 2000

Related U.S. Application Data

(63) Continuation-in-part of application No. 09/084,371, filed on May 27, 1998, now abandoned.

(51) Int. Cl.
*A61K 38/00* (2006.01)
*G01N 33/53* (2006.01)

(52) U.S. Cl. .................... 530/300; 514/2; 424/278.1; 435/7.1

(58) Field of Classification Search ................ 530/300, 530/350; 514/2; 424/278.1; 435/7.1
See application file for complete search history.

(56) References Cited

U.S. PATENT DOCUMENTS

| | | | | |
|---|---|---|---|---|
| 4,455,290 | A | 6/1984 | Olexa et al. | 424/1.1 |
| 5,292,362 | A | 3/1994 | Bass et al. | 106/124 |
| 5,428,014 | A | 6/1995 | Labroo et al. | 514/12 |
| 5,473,051 | A | 12/1995 | Altieri et al. | 530/382 |
| 5,599,790 | A | 2/1997 | Altieri et al. | 514/8 |
| 5,639,940 | A | 6/1997 | Garner et al. | 800/2 |
| 5,939,385 | A | 8/1999 | Labroo et al. | 514/12 |
| 6,083,902 | A | 7/2000 | Cederhom-Williams | 514/2 |
| 2004/0126758 | A1 | 7/2004 | Marx et al. | 435/6 |

FOREIGN PATENT DOCUMENTS

WO    WO 95/23868    *    9/1995
WO    WO 9961041 A1 *   12/1999

OTHER PUBLICATIONS

Watt, K. W. K. et al. (1979) Amino acid sequence of the beta chain of human fibrinogen. Biochemistry. vol. 18, pp. 68-76.*
Koopman, J. et al. (1992) Abnormal fibrinogens IJmuiden (B beta Arg14—Cys) and Nijmegen (B beta Arg44—Cys) form disulfide-linked fibrinogen-albumin complexes. Proc. Natl. Acad. Sci. U S A. vol. 89, pp. 3478-3482.*
Attachment 1: sequence alignment, pp. 1-3.*
Pandya et al. (1985) Conservation of human fibrinogen conformation after cleavage of the B beta chain NH2 terminus.☐☐J. Biol. Chem. vol. 260, pp. 2994-3000.*
Blumenstein et al. (1992) A beta-turn is present in the 392-411 segment of the human fibrinogen gamma-chain. Effects of structural changes in this segment on affinity to antibody 4A5. Biochemistry. vol. 31, pp. 10692-10698.*

Henschen et al. (1983) Covalent structure of fibrinogen. Ann. N. Y. Acad. Sci. vol. 408, pp. 28-43.*
Duga et al. (2000) Missense mutations in the human beta fibrinogen gene cause congenital afibrinogenemia by impairing fibrinogen secretion. Blood. vol. 95, pp. 1336-1341.*
Yee et al. (1997) Crystal structure of a 30 kDa C-terminal fragment from the gamma chain of human fibrinogen. Structure, vol. 5, pp. 125-138.*
Henschen et al. (1980) human fibrinogen sequence, sulfur bridge, glycosylation and some structural variants, in "Protides of the biological Fluids" Proc. 28th Colloq., Peeters, H., ed., pp. 51-56.*
Mayo et al. (1990) 1H NMR sequential assignments and secondary structure analysis of human fibrinogen gamma-chain C-terminal residues 385-411. Biochemistry, vol. 29, pp. 3277-3286.*
David R. Phillips et al., XP-002218130"The Platelet Membrane Glycoprotein IIb-IIIa Complex", The Journal of The American Society of Hematology, Blood, vol. 71, No. 4, pp. 831-843 (1988).
C.J. Nieman et al., XP-001118065, "A Colourimetric Enzyme-Linked Sandwich Assay For The Detection Of Human Platelets Bound To A Fibrinogen-Coated Surface", Thrombosis Research, vol. 62; pp. 189-197 (1991).
Yiping Fu et al., XP-002218053 "Fibrinogen α Genes: Conservation of Bipartite Transcripts and Carboxy-Terminal-Extended α Subunits in Vertebrates", GENOMICS, vol. 30, pp. 71-76 (1995).
W. D. Thompson et al., XP-000983610, "Angiogenic Activity Of Fibrin Degradation Products Is Located In Fibrin Fragment E", Department of Pathology and Clinical Biochemistry, Journal Of P Pathology. vol. 168, pp. 47-53 (1992).
Dominic W. Chung et al., "Characterization of Complementary Deoxyribonucleic Acid and Genomic Deoxyribonucleic Acid for the β Chain of Human Fibrinogen", American Chemical Society, Biochemistry, vol. 22, pp. 3244-3250 (1983).
Michael Blumenstein et al., "A β-Turn Is Present in the 392-411 Segment of the Human Fibrinogen γ-Chain.Effects of Structural Changes in This Segment on Affinity to Antibody 4A5", American Chemical Society, Biochemistry, vol. 31, pp. 10692-10698 (1992).
Yiping Fu et al., "Carboxy-Terminal-Extended Variant of the Human Fibrinogen α Subunit: A Novel Exon Conferring Marked Homology to β and γ Subunits", American Chemical Society, Biochemistry, vol. 31, pp. 11968-11972 (1992).
Cezary Watala et al., "Microenvironmental changes in platelet membranes induced by the interaction of fibrinogen-derived peptide ligands with platelet integrins", Eur. J. Biochem., vol. 235, pp. 281-288 (1996).

* cited by examiner

*Primary Examiner*—Jon Weber
*Assistant Examiner*—Samuel Wei Liu
(74) *Attorney, Agent, or Firm*—Winston & Strawn LLP

(57) ABSTRACT

This invention is related to a novel peptide consisting of the amino acid sequence of SEQ ID NO:1, and a pharmaceutical composition comprising the peptide thereof.

4 Claims, 7 Drawing Sheets

SEQUENCE LISTING

```
<160> NUMBER OF SEQ ID NOS: 12

<210> SEQ ID NO 1
<211> LENGTH: 21
<212> TYPE: PRT
<213> ORGANISM: Artificial
<220> FEATURE:
<223> OTHER INFORMATION: Equivalent to the c-terminus of fibrinogen
      beta-chain

<400> SEQUENCE: 1

Lys Gly Ser Trp Tyr Ser Met Arg Lys Met Ser Met Lys Ile Arg Pro
1               5                   10                  15

Phe Phe Pro Gln Gln
            20

<210> SEQ ID NO 2
<211> LENGTH: 20
<212> TYPE: PRT
<213> ORGANISM: Artificial
<220> FEATURE:
<223> OTHER INFORMATION: Equivalent to an internal sequence of
      fibrinogen gamma-chain

<400> SEQUENCE: 2

Lys Thr Arg Trp Tyr Ser Met Lys Lys Thr Thr Met Lys Ile Ile Pro
1               5                   10                  15

Phe Asn Arg Leu
            20

<210> SEQ ID NO 3
<211> LENGTH: 20
<212> TYPE: PRT
<213> ORGANISM: Artificial
<220> FEATURE:
<223> OTHER INFORMATION: Equivalent to the c-erminus of fibrinogen
      alpha-E-chain

<400> SEQUENCE: 3

Arg Gly Ala Asp Tyr Ser Leu Arg Ala Val Arg Met Lys Ile Arg Pro
1               5                   10                  15

Leu Val Thr Gln
            20

<210> SEQ ID NO 4
<211> LENGTH: 19
<212> TYPE: PRT
<213> ORGANISM: Artificial
<220> FEATURE:
<223> OTHER INFORMATION: Equivalent to the c-terminus of fibrinogen
      alpha-chain

<400> SEQUENCE: 4

Glu Ala Asp His Glu Gly Thr His Ser Thr Lys Arg Gly His Ala Lys
1               5                   10                  15

Ser Arg Pro

<210> SEQ ID NO 5
```

```
<211> LENGTH: 20
<212> TYPE: PRT
<213> ORGANISM: Artificial
<220> FEATURE:
<223> OTHER INFORMATION: Equivalent to the c-terminus of fibrinogen
      gamma-chain

<400> SEQUENCE: 5

Leu Thr Ile Gly Glu Gly Gln Gln His His Leu Gly Gly Ala Lys Gln
1               5                   10                  15

Ala Gly Asp Val
            20

<210> SEQ ID NO 6
<211> LENGTH: 29
<212> TYPE: PRT
<213> ORGANISM: Artificial
<220> FEATURE:
<223> OTHER INFORMATION: Fibrinogen C-beta consensus sequence
<220> FEATURE:
<221> NAME/KEY: MISC_FEATURE
<222> LOCATION: (1)..(2)
<223> OTHER INFORMATION: Xaa = Hydrophilic amino acid selected from Asp,
      Glu, His, Lys, Asn, Gln, Arg, Ser, Thr
<220> FEATURE:
<221> NAME/KEY: MISC_FEATURE
<222> LOCATION: (7)..(7)
<223> OTHER INFORMATION: Xaa = Hydrophobic amino acid selected from Ala,
      Phe, Ile, Leu, Met, Pro, Val, Trp, Tyr
<220> FEATURE:
<221> NAME/KEY: MISC_FEATURE
<222> LOCATION: (8)..(8)
<223> OTHER INFORMATION: Xaa = Hydrophilic amino acid selected from Asp,
      Glu, His, Lys, Asn, Gln, Arg, Ser, Thr
<220> FEATURE:
<221> NAME/KEY: MISC_FEATURE
<222> LOCATION: (9)..(9)
<223> OTHER INFORMATION: Xaa = Hydrophobic amino acid selected from Ala,
      Phe, Ile, Leu, Met, Pro, Val, Trp, Tyr
<220> FEATURE:
<221> NAME/KEY: MISC_FEATURE
<222> LOCATION: (10)..(10)
<223> OTHER INFORMATION: Xaa = Hydrophilic amino acid selected from Asp,
      Glu, His, Lys, Asn, Gln, Arg, Ser, Thr
<220> FEATURE:
<221> NAME/KEY: MISC_FEATURE
<222> LOCATION: (12)..(12)
<223> OTHER INFORMATION: Xaa = Ala or Ser
<220> FEATURE:
<221> NAME/KEY: MISC_FEATURE
<222> LOCATION: (13)..(13)
<223> OTHER INFORMATION: Xaa = Any amino acid
<220> FEATURE:
<221> NAME/KEY: MISC_FEATURE
<222> LOCATION: (16)..(16)
<223> OTHER INFORMATION: Xaa = Hydrophobic amino acid selected from Ala,
      Phe, Ile, Leu, Met, Pro, Val, Trp, Tyr
<220> FEATURE:
<221> NAME/KEY: MISC_FEATURE
<222> LOCATION: (18)..(18)
<223> OTHER INFORMATION: Xaa = Any amino acid
<220> FEATURE:
<221> NAME/KEY: MISC_FEATURE
<222> LOCATION: (19)..(19)
<223> OTHER INFORMATION: Xaa = Hydrophobic amino acid selected from Ala,
      Phe, Ile, Leu, Met, Pro, Val, Trp, Tyr
<220> FEATURE:
<221> NAME/KEY: MISC_FEATURE
<222> LOCATION: (20)..(20)
<223> OTHER INFORMATION: Xaa = Any amino acid
<220> FEATURE:
<221> NAME/KEY: MISC_FEATURE
<222> LOCATION: (26)..(28)
<223> OTHER INFORMATION: Xaa = Any amino acid

<400> SEQUENCE: 6
```

```
Xaa Xaa Gly Val Val Trp Xaa Xaa Xaa Xaa Gly Xaa Xaa Tyr Ser Xaa
1               5                   10                  15

Arg Xaa Xaa Xaa Met Lys Ile Arg Pro Xaa Xaa Xaa Gln
            20                  25
```

<210> SEQ ID NO 7
<211> LENGTH: 65
<212> TYPE: DNA
<213> ORGANISM: Artificial
<220> FEATURE:
<223> OTHER INFORMATION: Encodig haptotactic peptide C-beta

<400> SEQUENCE: 7

```
aagggtcat ggtatcaatg aggaagatga gtatgaagat caggcccttc ttcccacagc   60
aatag                                                              65
```

<210> SEQ ID NO 8
<211> LENGTH: 63
<212> TYPE: DNA
<213> ORGANISM: Artificial
<220> FEATURE:
<223> OTHER INFORMATION: Encoding haptotactic peptide C-alpha-E

<400> SEQUENCE: 8

```
agaggggcag attattccct cagggctgtt cgcatgaaaa ttaggcccct tgtgacccaa   60
tag                                                                63
```

<210> SEQ ID NO 9
<211> LENGTH: 63
<212> TYPE: DNA
<213> ORGANISM: Artificial
<220> FEATURE:
<223> OTHER INFORMATION: Encoding haptotactic peptide Pre-C-gamma

<400> SEQUENCE: 9

```
aaaacccggt ggtattccat gaagaaaacc actatgaaga taatcccatt caacagactc   60
aca                                                                63
```

<210> SEQ ID NO 10
<211> LENGTH: 15
<212> TYPE: PRT
<213> ORGANISM: Artificial
<220> FEATURE:
<223> OTHER INFORMATION: Haptotactic consensus sequence
<220> FEATURE:
<221> NAME/KEY: MISC_FEATURE
<222> LOCATION: (3)..(3)
<223> OTHER INFORMATION: Xaa is absent or hydrophobic amino acid
      selected from Ala, Phe, Ile, Leu, Met, Pro, Val, Trp, Tyr.
<220> FEATURE:
<221> NAME/KEY: MISC_FEATURE
<222> LOCATION: (5)..(5)
<223> OTHER INFORMATION: Xaa = Any amino acid or absent
<220> FEATURE:
<221> NAME/KEY: MISC_FEATURE
<222> LOCATION: (6)..(6)
<223> OTHER INFORMATION: Xaa is absent or hydrophobic amino acid
      selected from Ala, Phe, Ile, Leu, Met, Pro, Val, Trp, Tyr
<220> FEATURE:
<221> NAME/KEY: MISC_FEATURE
<222> LOCATION: (12)..(14)
<223> OTHER INFORMATION: Xaa = Any amino acid or absent

<400> SEQUENCE: 10

```
Tyr Ser Xaa Arg Xaa Xaa Met Lys Ile Arg Pro Xaa Xaa Xaa Gln
1               5                   10                  15
```

```
<210> SEQ ID NO 11
<211> LENGTH: 20
<212> TYPE: PRT
<213> ORGANISM: Artificial
<220> FEATURE:
<223> OTHER INFORMATION: Haptotactic consensus sequence
<220> FEATURE:
<221> NAME/KEY: MISC_FEATURE
<222> LOCATION: (2)..(3)
<223> OTHER INFORMATION: Xaa = Any amino acid or absent
<220> FEATURE:
<221> NAME/KEY: MISC_FEATURE
<222> LOCATION: (8)..(8)
<223> OTHER INFORMATION: Xaa is absent or hydrophilic amino acid
      selected from Asp, Glu, His, Lys, Asn, Gln, Arg, Ser, Thr
<220> FEATURE:
<221> NAME/KEY: MISC_FEATURE
<222> LOCATION: (10)..(10)
<223> OTHER INFORMATION: Xaa = Any amino acid or absent
<220> FEATURE:
<221> NAME/KEY: MISC_FEATURE
<222> LOCATION: (11)..(11)
<223> OTHER INFORMATION: Xaa is absent or hydrophilic amino acid
      selected from Asp, Glu, His, Lys, Asn, Gln, Arg, Ser, Thr
<220> FEATURE:
<221> NAME/KEY: MISC_FEATURE
<222> LOCATION: (15)..(15)
<223> OTHER INFORMATION: Xaa = Any amino acid or absent
<220> FEATURE:
<221> NAME/KEY: MISC_FEATURE
<222> LOCATION: (18)..(20)
<223> OTHER INFORMATION: Xaa = Any amino acid or absent

<400> SEQUENCE: 11

Lys Xaa Xaa Trp Tyr Ser Met Xaa Lys Xaa Xaa Met Lys Ile Xaa Pro
 1               5                   10                  15

Phe Xaa Xaa Xaa
            20

<210> SEQ ID NO 12
<211> LENGTH: 30
<212> TYPE: PRT
<213> ORGANISM: Artificial
<220> FEATURE:
<223> OTHER INFORMATION: Fibrinogen C beta homology sequence
<220> FEATURE:
<221> NAME/KEY: MISC_FEATURE
<222> LOCATION: (2)..(2)
<223> OTHER INFORMATION: Xaa = Hydrophilic amino acid selected from Asp,
      Glu, His, Lys, Asn, Gln, Arg, Ser, Thr
<220> FEATURE:
<221> NAME/KEY: MISC_FEATURE
<222> LOCATION: (4)..(5)
<223> OTHER INFORMATION: Xaa = Hydrophobic amino acid selected from Ala,
      Phe, Ile, Leu, Met, Pro, Val, Trp, Tyr
<220> FEATURE:
<221> NAME/KEY: MISC_FEATURE
<222> LOCATION: (7)..(8)
<223> OTHER INFORMATION: Xaa = Any amino acid
<220> FEATURE:
<221> NAME/KEY: MISC_FEATURE
<222> LOCATION: (11)..(12)
<223> OTHER INFORMATION: Xaa = Any amino acid
<220> FEATURE:
<221> NAME/KEY: MISC_FEATURE
<222> LOCATION: (17)..(17)
<223> OTHER INFORMATION: Xaa = Hydrophilic amino acid selected from Asp,
      Glu, His, Lys, Asn, Gln, Arg, Ser, Thr
<220> FEATURE:
<221> NAME/KEY: MISC_FEATURE
<222> LOCATION: (19)..(19)
<223> OTHER INFORMATION: Xaa = Any amino acid
<220> FEATURE:
<221> NAME/KEY: MISC_FEATURE
```

```
-continued

<222> LOCATION: (20)..(20)
<223> OTHER INFORMATION: Xaa = Hydrophilic amino acid selected from Asp,
      Glu, His, Lys, Asn, Gln, Arg, Ser, Thr
<220> FEATURE:
<221> NAME/KEY: MISC_FEATURE
<222> LOCATION: (24)..(24)
<223> OTHER INFORMATION: Xaa = Any amino acid
<220> FEATURE:
<221> NAME/KEY: MISC_FEATURE
<222> LOCATION: (27)..(30)
<223> OTHER INFORMATION: Xaa = Any amino acid

<400> SEQUENCE: 12

Asp Xaa Gly Xaa Xaa Trp Xaa Xaa Trp Lys Xaa Xaa Trp Tyr Ser Met
1               5                   10                  15

Xaa Lys Xaa Xaa Met Lys Ile Xaa Pro Phe Xaa Xaa Xaa Xaa
            20                  25                  30
```

HAPTOTACTIC PEPTIDES

CROSS REFERENCE TO RELATED APPLICATIONS

This application is a continuation-in-part of application Ser. No. 09/084,371, filed May 27, 1998 now abandoned, the content of which are incorporated by reference in their entirety.

FIELD AND BACKGROUND

The present invention relates to novel haptotactic peptides, and in particular, to novel peptides which are homologous to a portion of the carboxy termini of fibrinogen chains, as well as to potential uses for these peptides.

Fibrinogen is the plasma protein which forms the clot when blood coagulates. Many studies have been conducted on the amino acid sequences and structure of fibrinogen (Mosesson, M. and Doolittle, R. (Eds.) "The biology of fibrinogen and fibrin", Ann. N.Y. Acad. Sci., 408, 1983, Henschen, A. et al., "Structure of fibrinogen", Ann. N.Y. Acad. Sci., 408, 1983, Spraggon, G. et al., "Crystal structure of fragment D from human fibrinogen and its crosslinked counterpart from fibrin", Nature. 389:455–462, 1997, Murakawa, M. et al., "Diversity of primary structures of the carboxy-terminal regions of mammalian fibrinogen Aα-chains", Thromb. & Haemostat., 69:351–360, 1993). Normally, fibrinogen itself has a molecular weight of 340 kDa and is constructed from two sets of three peptide chains, named α, β, and γ. The constituent chains of fibrinogen are highly conserved between species. Recent work has also described a fibrinogen protein with a longer α chain, called αE fibrinogen, which has a concomitantly higher molecular weight of 420 kDa and which may play a role in development (Fu, Y. and Grieninger, G. "Fib420: A normal human variant of fibrinogen with two extended α chains". Proc. Natl. Acad. Sci. USA. 91: 2625–2628, (1994), Fu, Y. et al., "Carboxy-terminal-extended variant of the human fibrinogen α subunit: A novel exon conferring marked homology to β and γ subunits" Biochem., 31:11968–11972, (1992)). Thus, these four types of fibrinogen chains, α, β, γ and αE, have 610, 410, 391 and 1096 amino acids, respectively (numbering based on the Gene-bank data base at info@ncbi.nlm.nih.gov).

Fibrin clots are formed in vivo at the sites of tissue injury based upon the reaction of fibrinogen and thrombin in the presence of calcium ions. These clots have a major role in hemostasis. After clot formation, fibrin serves a provisional matrix for cell recruitment into the wound bed. Normally, the earliest cells mobilized into the wound bed are inflammatory, such as leukocytes and particularly macrophages. Concomitant With their penetration into the fibrin, these inflammatory cells participate in lysing the fibrin by generating plasmin, metallo-proteinases (MIPs) and/or free radicals. Thus, the wound bed contains substantial quantities of peptides A and B (FPA and FPB) released by thrombin during the onset of coagulation and numerous fibrin breakdown products are generated by lytic enzymes or free-radicals (Gray, A. J., Reeves, J. T., Harrison, N. K., Winlove, P. and Laurent, G. J., "Growth factors for human fibroblasts in the solute remaining after clot formation", J. Cell Sci., 96: 271–274, (1990), Marx G. "Immunological monitoring of Fenton fragmentation of fibrinogen". Free Radicals Res. Comm. 12: 517–520 (1991), Francis, C. W., Marder, V. J. and Barlow, G. H., "Plasmic degradation of crosslinked fibrin". J. Clin Invest., 66: 1033–1043, (1980), Cottrell, B. A. and Doolittle, R. F. "The amino acid sequence of a 27-residue peptide released from α-chain carboxy-terminus during the plasmic digestion of human fibrinogen", Acad. Press., 71: 754–766, (1976)).

Subsequently, the inflammatory cells are followed by the migration of cells of the mesenchymal cell lineage such as fibroblasts which further digest fibrin, replacing it with extracellular matrix (ECM). Endothelial cells also infiltrate the wound bed and generate microcapillary structures. Ultimately these cells replace the provisional fibrin matrix with granulation tissue populated by parenchymal cells and vasculature within the newly synthesized ECM.

The attachment and migratory responses of cells to matrix were proposed to be controlled mainly by specific receptors (integrins) or by intercellular adhesion molecules (ICAM) that interact with cell membrane receptors which subsequently induce either migratory reactions or cell adhesion to matrix. These interactions may trigger other regulatory mechanisms of cell activity, such as shape change or proliferation. Growth factors and cytokines activate such cell receptors by binding to them, and thus, trigger cellular responses (Ruslahti, E. (1996) RGD and other recognition sequences for integrins. Ann. Rev. Cell Dev. Biol. 12, 697–715 and Hynes, R. O. (1992) Integrins: Versatility, modulation and signaling in cell adhesion. Cell 69, 11–25).

Cytokines of different classes regulate cellular activity and responses, control cell survival, growth and differentiation. Excluding classical endocrine hormones, cytokines encompass those families of cell regulators variously known as growth factors, interleukins, lymphokines and interferons.

All previously described cytokines are composed of more than 50 amino acids (aa); most are over 100 aa long. Based on X-ray crystallography, cytokines exhibit 8 structural groups (Nathan C. & Sporn M., "Cytokines in context", J. Cell. Biol. 113: 981–986 (1991)) and bind to a variety of cellular receptors such as integrins or interferon receptors. Binding to cell receptors triggers a cascade of events leading to intra-cellular phosphorylation of proteins, which is transduced into gene expression, cell proliferation, cell differentiation, changes in cell shape, motility and apoptosis. Thus, cytokines play an important role in physiological processes such as development and wound healing.

Human fibroblasts are the major cellular entities responsible for the regeneration of the extracellular matrix Within the wound bed. Human fibroblasts also express specific membrane receptors to fibrinogen and thrombin. In the case of skin wounds, human fibroblasts reform the matrix of the dermis. For example, during the course of healing of an incisional skin wound, human fibroblasts are mobilized from the surrounding tissue and enter into the fibrin clot, help to dissolve the clot, and then generate as well as reform the collagen in the extracellular matrix. Based upon these properties of human fibroblasts, fibroblast implants have been suggested to supplement the process of healing in damaged skin (Gorodetsky, R. et al., Radiat. Res. 125:181–186, 1991).

One material used for this purpose is benzoylated hyaluronic acid (HA) sheets containing holes or pores as a carrier for fibroblasts and keratinocytes for wound healing (Andreassi, L., et al., Wounds, 3:116–126, 1991). Specifically, HA sheets were cultured with such cells which grow within the pore structure. The HA sheets were then affixed to the site of the burn injury, where the cells migrated out of the sheet and ultimately accelerated the rate of wound re-granulation. A major problem with implanted HA sheets, however, is that they are not metabolized by tissue, are mechanically cumbersome to administer, and may cause undesired immunological effects in the long term.

Another material used for prosthetic tissue engineering is collagen from pig or beef sources. However, collagen has several mechanical limitations and may reduce the new collagen synthesis by cells that are incorporated in it. There is also concern regarding the safety of animal collagen products for medical implantation and its use has been severely limited in Europe.

Fibrin microbeads (FMB) have been disclosed as possessing both chemotactic and proliferative effects for certain types of cells in U.S. application Ser. No. 08/934,283, filed in Sep. 19, 1997 and Gorodetsky, R., Vexler A., Shamir M., An J., Levdansky L., and Marx G. (1999). J. Invest. Dermatol. 112, 866–872 (1999)). The cells that are attracted to FMB include fibroblasts and smooth muscle endothelial cells, but typically not keratinocytes. The cells were shown to migrate into these FMB by chemotaxis, attach to them (haptotaxis) and then to proliferate on the FMB. Furthermore, the cells were shown to remain stable for prolonged periods of time when cultured within the FMB. Thus, the disclosed FMB appeared to stimulate both cell chemotaxis, haptotaxis and cell growth.

However, the fibrin microbeads themselves have certain inherent limitations. For example, the FMB are particularly useful only as three-dimensional micro-structures. If other structures were desired, and in particular if the lack of such was desired, FMB would not be particularly useful Furthermore, FMB would not be particularly useful for avoiding the use of blood plasma proteins.

A more useful approach would identify the epitopes of fibrin(ogen) responsible for its chemotactic and haptotactic properties. Attempts have been made to find these small epitopes within the larger fibrin(ogen) molecule. A voluminous literature exists which describes the binding of fibrinogen ($\gamma$400–411) to platelets through the GPIIb/IIa receptor (see for example Savage B., Bottini E. & Ruggeri Z M., "Interaction of integrin alpha IIb beta with multiple fibrinogen domains during platelet adhesion", *J. Biol. Chem.* 270: 28812–7 (1995)), and the aggregation activity of the amino B$\beta$ 15–42 terminus which is exposed after release of fibrinopeptide B. In addition, a peptide containing the 16 amino acids of the sequence of the $\gamma$-carboxy terminus of fibrinogen was synthesized and was found to bind to platelet integrin (D'Souza, S. E. et al., *J. Biol. Chem.*, 265:3440–3446, 1990). However, the biological activities of only a few other fibrinogen breakdown products have been investigated with cells and the activity of these different breakdown products seems to be widely variable.

In another example, fibrinogen fragment E was reported to exhibit angiogenic properties and to inhibit endothelial cell migration in a Boyden chamber chemotactic assay (Thompson, W. D., Smith, E. B., Stirk, C. M., Marshall, F. I., Stout, A. J. and Kocchar, A., "Angiogenic activity of fibrin degradation products is located in fibrin fragment E", *J. Pathol.* 168: 47–53 (1992)). Fragment D was reported to cause detachment of cultured endothelial cells from the extracellular matrix (ECM) substratum in a process which was both concentration and time dependent (Savage B., Bottini E. & Ruggeri Z M., "Interaction of integrin alpha IIb beta with multiple fibrinogen domains during platelet adhesion", *J. Biol. Chem.* 270: 28812–7 (1995)). Isolated constituent chains of fibrinogen (A$\alpha$1, A$\alpha$2 and B$\beta$) released upon activation of the fibrinogen by thrombin were observed to stimulate fibroblast proliferation by 23–31% above controls whereas isolated $\gamma$ chain had no effect (Gray. A. J., Bishop, J. E., Reeves, J. T. and Laurent, G. J.; "A$\alpha$ and B$\beta$ Chains of fibrinogen stimulate proliferation of human fibroblasts", *J. Cell Sci.*, 104: 409–413, (1993)). Human polymorphonuclear leukocytes (PMN) were shown to bind to fibrin(ogen) coated surfaces via a type 3 (CD11b/CD18) complement receptor homologous to the GPIIb/IIIa receptor through a decamer of the $\gamma$ chain carboxy terminus (LG-GAKQAGDV). Vasoactive peptides corresponding to residues 43–47 of the B$\beta$ chain and 220–230 of the A$\alpha$ chain were identified (Gray A. J., Bishop, J. E., Reeves, J. T. and Laurent, G. J.; "A$\alpha$ and B$\beta$ Chains of fibrinogen stimulate proliferation of human fibroblasts", *J. Cell Sci.*, 104: 409–413, (1993)).

The biological activities of only few other fibrinogen breakdown products have been investigated, whose cellular activity seems to be widely variable (Saldeen T: Vasoactive peptides derived from degradation of Fibrinogen and fibrin. Proc. NY Acad Sci USA, 408: 424–431 (1983)).

Fibrinogen itself when bound to sepharose beads, did not significantly affect cell proliferation, but elicited haplotactic/attachment reactions from human (HF) or mouse (MF) fibroblasts, endothelial cells (EC) and smooth muscle (SMC) cells. Thrombin treatment of fibrinogen-sepharose beads (SB-fib), which would not affect the carboxy termini of the molecule, did not alter cellular responses, though plasmin, which clips off gamma carboxy termini and digests D-domain sequences, nearly totally abrogated the cell-attractant properties of SB-fib (Gorodetsky R., Vexler A., An J., Mou X, Marx G. (1998) J. Lab. Clin. Med. 131: 269–280).

Specific epitopes on fibrinogen have been hypothesized to express cell binding (haptotactic) properties. However, the amino acid sequence(s) of such putative haptotactic epitopes have not yet been specified. The identification of such epitopes would have a number of applications, enabling more specific intervention in the wound healing process and in the development of novel therapeutic compositions or devices. Furthermore, novel diagnostic tests for testing cellular haptotactic responses could potentially be developed. Thus, the identification of these specific epitopes or peptides exhibiting cellular activity would have great utility.

There is thus a recognized need for, and it would be highly advantageous to have, a peptide or peptides with specifically determined cellular effects, such as cell proliferative or chemotactic or haptotactic properties, which do not require the presence of the entirety of the fibrin molecule to exert cellular effects.

SUMMARY OF THE INVENTION

It is one object of the present invention to provide haptotactic peptides with novel amino acid sequences which are featured within the carboxy termini of fibrinogen.

It is another object of the present invention to provide such peptides useful for pharmaceutical compositions.

It is still another object of the present invention to provide such haptotactic peptides useful for cell culture and cell separation.

It is yet another object of the present invention to provide such haptotactic peptides useful for novel cell structures, including biomedical devices.

These and other objects of the present invention are explained in greater detail in the descriptions, Figures and claims below.

The novel synthetic peptide sequences of the present invention are homologous to selected regions present within the fibrin molecule, yet retain certain derived properties of the entire molecule, such as cell adhesive effects, for example. The specific sequences of these haptotactic peptides are KGSWYSMRKMSMKIRPFFPQQ (peptide-Cβ (code name-(09), hereinafter referred to as 'peptide-Cβ', (SEQ ID NO:1)), KTRWYSMKKTTMKIIPFNRL (peptide preCγ, (code name 70a, hereinafter referred to as 'peptide preCγ', (SEQ ID NO:2)) and RGADYSLRAVRMKIR-PLVTQ (peptide-CαE, (code name (71), hereinafter referred to as peptide-CαE, (SEQ ID NO:3)).

According to the teachings of the present invention, there is provided a synthetic polypeptide, comprising an amino acid sequence as set forth in SEQ ID NO:1. There is also provided a synthetic polypeptide, comprising an amino acid sequence as set forth in SEQ ID NO:2. There is also provided a synthetic polypeptide, comprising an amino acid sequence as set forth in SEQ ID NO:3. In addition, there is provided a polypeptide, comprising an amino acid sequence as set forth in SEQ ID NO:1 and functional analogues thereof having at least one amino acid substitution into a naturally occurring or non-naturally occurring amino acid and having a haptotactic activity. There is provided a polypeptide, comprising an amino acid sequence as set forth in SEQ ID NO:2 and functional analogues thereof having at least one amino acid substitution into a naturally occurring or non-naturally occurring amino acid and having a haptotactic activity. There is also provided a polypeptide, comprising an amino acid sequence as set forth in SEQ ID NO:3 and functional analogues thereof having at least one amino acid substitution into a naturally occurring or non-naturally occurring amino acid and having a haptotactic activity.

According to another embodiment there is provided an isolated nucleic acid comprising a polynucleotide encoding a polypeptide as set forth in SEQ ID NO:1. There is also provided an isolated nucleic acid comprising a polynucleotide encoding a polypetide as set forth in SEQ ID NO:2. Additionally, there is provided an isolated nucleic acid comprising a polynucleotide encoding a polypetide as set forth in SEQ ID NO:3.

According to another embodiment of the present invention, there is provided a composition, comprising a haptotactic peptide having a sequence selected from the group consisting of SEQ ID NO:1, SEQ ID NO:2 and SEQ ID NO:3. Preferably, the composition further comprises a pharmaceutically acceptable carrier. Also preferably, the composition further comprises a biological agent selected from the group consisting of drugs, vitamins, vitamin derivatives, growth factors, glucocorticosteroids, steroids, antibiotics, toxins, enzymes, enzyme inhibitors, immunomodulators, immunoglobulins and fragments thereof, fatty acid derivatives, polysaccharides, cell receptor binding molecules, anti-inflammatories, nucleic acids, and polynucleotides.

In a preferred embodiment the haptotactic peptide is attached to the surface of a prosthetic device.

In a preferred embodiment the haptotactic peptide is attached to a bead.

In a preferred embodiment the haptotactic peptide is attached to a matrix.

According to preferred embodiments of the present invention, the composition further comprises a cell selected from the group consisting of fibroblasts, endothelial cells, chondrocytes, osteoblasts, neuroblastoma cells, kidney cells, liver cells, pancreatic cells, thyroid cells, glial cells, nerve cells, smooth muscle cells, mouse mammary carcinoma cells, bone or cartilage forming cells, and combinations thereof.

According to yet another embodiment of the present invention, there is provided a cell structure, comprising: (a) a peptide having a sequence selected from the group consisting of SEQ ID NO:1, SEQ ID NO:2 and SEQ ID NO:3; (b) a cell bound to the peptide; and (c) a structure for supporting the cell, the peptide being attached to the structure such that the cell is supported by the structure. Preferably, the structure is a biomedical device.

According to another embodiment of the present invention, there is provided a polymer composition, comprising: (a) a plurality of subunits, each subunit featuring at least one haptotactic peptide selected from the group consisting of SEQ ID NO:1, SEQ ID NO:2 and SEQ ID NO:3; and (b) a plurality of linker moieties for attaching each of the plurality subunits to another of the plurality of subunits to form the polymer. Preferably, the subunit is comprised of the at least one haptotactic peptide, such that the polymer is a peptide polymer. Alternatively and preferably, the at least one haptotactic peptide is attached to the subunit, such that the polymer is a co-polymer.

Hereinafter, the term "wound-healing cells" refers to those cells which promote healing of a wound, including, but not limited to, fibroblasts, smooth muscle endothelial cells osteoblasts and chondrocytes.

The term "fibrin(ogen)" is known in the art as a mixture of fibrin and fibrinogen, and is referred to herein according to this definition. Hereinafter, the term "biologically active" refers to molecules, or complexes thereof, which are capable of exerting an effect in a biological system. Hereinafter, the term "fragment" refers to a portion of a molecule or a complex thereof, in which the portion includes substantially less than the entirety of the molecule or the complex thereof.

Hereinafter, the term "amino acid" refers to both natural and synthetic molecules which are capable of forming a peptidic bond with another such molecule. Hereinafter, the term "natural amino acid" refers to all naturally occurring amino acids, including both regular and non-regular natural amino acids. Hereinafter, the term "regular natural amino acid" refers to those amino acids which are normally used as components of a protein. Hereinafter, the term "non-regular natural amino acid" refers to naturally occurring amino acids produced by mammalian or non-mammalian eukaryotes, or by prokaryotes, which are not usually used as a component of a protein by eukaryotes or prokaryotes. Hereinafter, the term "synthetic amino acid" refers to all molecules which are artificially produced and which do not occur naturally in eukaryotes or prokaryotes, but which fulfill the required characteristics of an amino acid as defined above. Hereinafter, the term "peptide" includes both a chain of a sequence of amino acids, and analogues and mimetics having substantially similar or identical functionality thereof, including analogues having synthetic and natural amino acids. As shown in Table 1 below, peptide-Cα (code name peptide (07, hereinafter referred to as 'peptide-Cα', SEQ ID NO:4) has the amino acid sequence of the C-terminus of the alpha chain of fibrinogen.

BRIEF DESCRIPTION OF THE DRAWINGS

The invention is herein described, by way of example only, with reference to the accompanying drawings, wherein:

FIG. 5A shows the rate of binding of Cβ$^{FITC}$ (SEQ ID NO:1) and CαE$^{FITC}$ (SEQ ID NO:3) showing fast equilibrium within 5 minutes. FIG. 5B shows a dose response of Cβ$^{FITC}$ (SEQ ID NO:1) and CαE$^{FITC}$ (SEQ ID NO:3) showing binding to HF and BAEC in concentrations of up to 40 μM, assayed after incubation for 1 hr with peptides at 4° C. FIG. 5C shows the effect of elevated concentrations of unlabeled Cβ (SEQ ID NO:1) on the uptake of Cβ$^{FITC}$.

BRIEF DESCRIPTION OF THE INVENTION

The present invention relates to novel peptides, and in particular, to their corresponding novel peptide amino acid sequences, as well as to potential uses for these sequences. For example, these peptide sequences have potential medical uses, such as for therapeutic and diagnostic uses. The synthetic peptide sequences are homologous to regions of the fibrin molecule, yet retain certain desired properties of the entire molecule, such as cell adhesive effects, for example.

In particular, these haptotactic peptides are composed of a sequence homologous to 19–21 amino acids sequence at the carboxy terminus of the β chain (termed Cβ or code 09, (SEQ ID NO:1)) and a sequence (termed CαE or code 71, (SEQ ID NO:3)) homologous to the C-terminus sequence of the recently discovered αE chain, the so-called extended αE segment (αE) (Fu, Y. and Grieninger, G. "Fib$_{420}$: A normal human variant of fibrinogen with two extended a chains," Natl. Acad. Sci. USA, 91:2625–2628, (1994)). Additionally, is included preCγ (70A) (SEQ ID NO:2), a 20 mer peptide homologous to the internal γ-chain fibrinogen chain sequence at address γ373–392 (411 total) (termed preCγ or code 70A). Two other 19–21-mer peptides homologous to the C-termini of the α and the γ chains (termed Cα or code 07 (SEQ ID NO:4) and Cγ or code 71 (SEQ ID NO:5) respectively) are described and used as controls for haptotactic tests. Sequences of these peptides are given in Table 1 below.

Table 1 shows the names, codes and sequences of five peptides synthesized and tested, of which only Cβ (SEQ ID NO:1), CαE (SEQ ID NO:3) and PreCγ (SEQ ID NO:2) elicited significant haptotactic responses from cells. The haptotactic Cβ (SEQ ID NO:1), CαE (SEQ ID NO:3) and PreCγ (SEQ ID NO:2) peptides are homologous to each other as shown in bold (sequence numbering according to the database of the Swiss Gene bank);

TABLE 1

Synthetic peptides corresponding to the carboxy termini of fibrinogen.

| Name Code # | Chain Address | Sequence |
|---|---|---|
| Cα (07) (SEQ ID NO:4) | α 591–610 | EADHEGTHSTKRGHAKSRP |
| Cβ (09) (SEQ ID NO:1) | β 441–461 | KGSWYSMRKMSMKIRPFFPQQ |
| Cγ (70) (SEQ ID NO:5) | γ 392–411 | LTIGEGQQHHLGGAKQAGDV |
| PreCγ (70A) (SEQ ID NO:2) | γ 373–392 | KTRWYSMKKTTMKIIPFNRL |
| CαE (71) (SEQ ID NO:3) | αE 828–847 | RGADYSLRAVRMKIRPLVTQ |

Hereinafter, the term "haptotactic peptide" refers to peptides—Cβ (SEQ ID NO:1), CαE (SEQ ID NO:3) or preCγ (SEQ ID NO:2), having a sequence selected from the group consisting of: KGSWYSMRKMSMKIRPFFPQQ (SEQ ID NO:1), KTRWYSMKKTTMKIIPFNRL (SEQ ID NO:2) or RGADYSLRAVRMKIRPLVTQ (SEQ ID NO:3); as well as to analogues, derivatives, equivalents or peptido-mimetics thereof, displaying substantially identical or similar functional activity as one of the above-listed sequences. Peptides Cβ (SEQ ID NO:1) and preCγ (SEQ ID NO:2) elicited the greatest haptotactic activity, followed by peptide CαE (SEQ ID NO:3).

Figure 2:
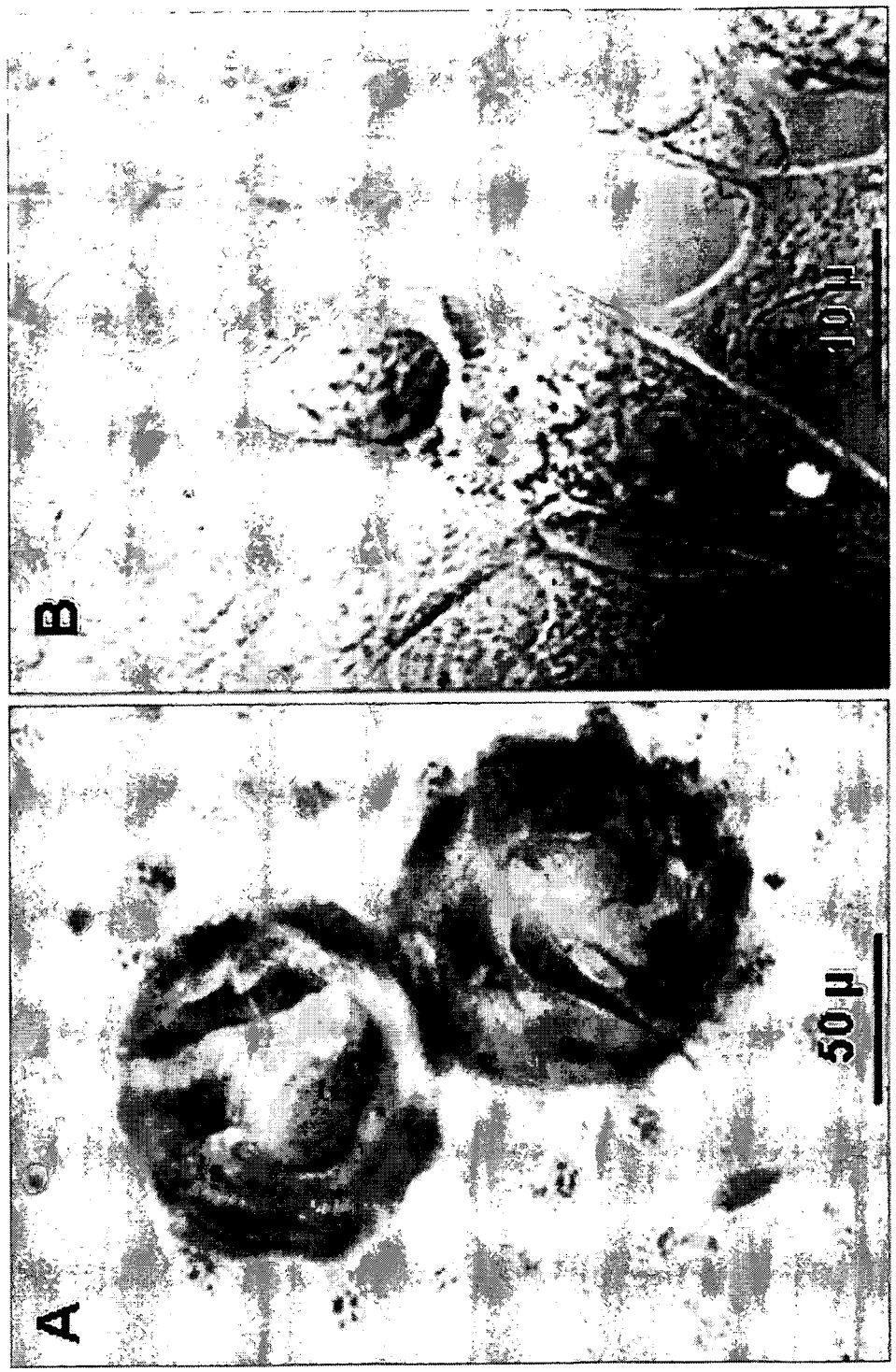
FIG. 2A shows the attachment and mounting of BAEC onto SB-Cβ (SEQ ID NO:1) visualized by light microscopy after 2 days of incubation with a nearly confluent culture. The cells on Sepharose beads (SB) were fixed and stained by Giemsa (objective x40). The attraction and adhesive response of the cells that mounted on the SB-Cβ (SEQ ID NO:1) is evident.
FIG. 2B shows phagocytosis of small chopped fragments of SB-Cβ$^{FITC}$ (SEQ ID NO:1) (approx. 1–5 μm in diameter) as viewed in an intracellular planar section in the middle of the cells by fluorescent confocal microscopy and Numarski optics. This shows that neutral materials can be rendered so attractive by the peptides that they become engulfed (phagocytosis) by the cell.

The mitogenic effects of these peptides were tested in cell culture systems. No effects on cell number were observed with any of these peptides These peptides were also evaluated for their cell adhesive properties when bound to sepharose beads (SB) placed on nearly confluent cell cultures. Specifically, peptides Cβ (SEQ ID NO:1) and preCγ (SEQ ID NO:2) elicited the greatest haptotactic response to EC, followed by the CαE peptide (SEQ ID NO:3) (FIG. 2, Table 3). The relative haptotactic activity of these peptides varies with the cell types By contrast, peptide-Cα (SEQ ID NO:4) elicited no cell adhesive effects and Cγ (SEQ ID NO:5) showed only negligible effect with EC that varied with the number of cell passages.

Two of the most potent peptides, peptides Cβ (SEQ ID NO:1) and CαE (SEQ ID NO:3), share an underlined sequence of YSXRXXMKIRPXXXQ (SEQ ID NO:10). The shared sequence itself, possibly with the addition of a spacer moiety or moieties for proper geometrical configuration, is also contemplated as a peptide of the present invention.

The two active peptides, peptides Cβ (SEQ ID NO:1) and preCγ (SEQ ID NO:2) show marked homology and share an underlined sequence of KXXWYSMXKXXMKIXPFXXX (SEQ ID NO:11) as is shown in Table 1.

Three synthetic peptides, homologues of the C-termini chain sequences of fibrinogen, Cβ (SEQ ID NO:1), CαE (SEQ ID NO:3) and preCγ (SEQ ID NO:2) were active towards cells and are well conserved in evolution (Table 2). Other sequences with this same homology are also potentially active. Without wishing to be limited by a single mechanism, functional cell attachment features of fibrinogen chains are critical to the normal development and wound healing of all species.

Table 2 shows interspecies homology and sequence conservation of the active C-termini sequences of the fibrinogen Cβ (SEQ ID NO:1), the CαE (SEQ ID NO:3) and the PreCγ (SEQ ID NO:2). Shaded areas represent the homologous sequences. It has been shown that there is a chain of amino acids having a fibrinogen Cβ consensus sequence of ++GVVW++++G+-YS+R-+-MKIRP---Q (SEQ ID NO:6). The + sign denotes similar amino acids and the - sign indicates dissimilar amino acids. In addition there is a chain of amino acids having a fibrinogen Cβ homology sequence of D+G++W--WK--WK--WYSM+K-+MKI-PF---- (SEQ ID NO:12). The high statistical significance of these conserved sequences suggests that these sequences confer haptotactic activity to fibrinogen in all species:

TABLE 2

| Peptide name and Source | Additional pre-termini sequences (not tested) | Examined C-termini peptide sequences |
|---|---|---|
| | ? | ?? ? |

A. Homology of human Cβ to other species

| Human (Cβ) | T D D G V V W M N W | K G S W Y S M R K M S M K I R P F F |
|---|---|---|
| Rat | T D D G V V W M N W | K G S W Y S R R R M S M K I R P V F |
| Bovine | T D D G V V W M N W | Q G S W Y S M K K M S M K I R P Y F |
| Chicken | T D D G T V W M N W | K G S W Y S M K K M S M K I K P Y F |
| Lamprey | T D D G V V W M N W | K G S W Y S M R Q M A M K L R P K W |

B. Homology of human CαE to other species and comparison to human Cβ

| Human | E N G V V W V S F | R G A D Y S L R A V R M K I R P L V |
|---|---|---|
| Rat | E N G V L W I P F | R G A D Y S L W A V R M K I R P L V |
| Chicken | E N G V V W I P F | R A S D Y S L K V V R M K I R P L E |
| Wood Frog | E N G V V W L S F | K P D D Y S L K T V K M K I R P M E |
| Rabbit | E N G V V W V P F | R G A D Y S L R A V R | | | | | | |

| Homology to Cβ | + + G V V W + + + | + G + - Y S + R - + - M K I R P - - |

C. Homology of human preCγ to other species and comparison to human Cβ

| Human | D N G I I W A T W | K T R W Y S M K K T T M K I I P F N |
|---|---|---|
| Rat | D N G I I W A T W | K T R W Y S M K E T T M K I I P F N |
| Ferret | D N G I I W A T W | K Q S W Y S M K K T T M K I I P F N |
| Chicken | D N G I I W A T W | R D R W Y S M K K T T M K I I P F N |
| Bovine | D N G I I W A T W | K S R W Y S M K K T T M K I I P F N |
| Wood Frog | D N G I I W V T F | R T R W Y S M M K T S M K I I P F N |
| Xenopus Frog | D N G I I W A T W | R R R W Y S M K S V T M K I M P L N |
| Carp-fish (C-frag) | L I I W V T F | R T R W Y S M K E T T M K I I P I N |
| Lamprey | D D L I I W V T W | H D R W Y S L K M T T M K L L P M G |

| Homology to Cβ | D - G + + W - - W | K - - W Y S M + K - - M K I - P F - |

▓, [X or +] & [X or -] Full, partial and no homology, respectively (*) - Full and partially matched residues
(**) - Proportion of full or partial match within the homologous sequences of the 27–30mer C-termini of the tested chains
The peptides synthesized and tested were analogues to the human sequences in the range indicated by 2 arrows at the top of the table.
P-values describe the probability for random match.

The DNA and RNA sequences that code for the amino acids of the haptotactic peptides were deduced. Without wishing to be limited, one example of DNA sequences that code for the amino acids of the haptotactic peptides is as follows:

Cβ—DNA (SEQ ID NO:7) AAGGGGTCATGGTACT-CAATGAGGAAGATGAGTATGAAGATCAGGCCC TTCTTCCCACAGCAA TAG

CαE—DNA (SEQ ID NO:8) AGAGGGGCAGATTAT-TCCCTCAGGGCTGTTCGCATGAAAATTAGGCCC CTTGTGACCCAA TAG

PreCγ—DNA (SEQ ID NO:9) AAAACCCGGTGGTAT-TCCATGAAGAAAACCACTATGAAGA,rAAT000AT TCAACAGACTCACA

The amino acids of the haptotactic peptides can be encoded by other DNA sequences.

The DNA and RNA sequences that code for the amino acids of the haptotactic peptides can be used for medical as well as diagnostic purposes. The haptotactic peptides of the present invention are contemplated for many different uses. Therapeutic uses include, but are not limited to, treatment of a wound bed. Methods for treatment of the wound bed with the peptides of the present invention are given in greater detail in Example 7 below. In addition, therapeutic compositions which include the peptides of the present invention are given in greater detail in Example 6 below.

Additional uses of the haptotactic peptides of the present invention include, but are not limited to, the growth and transport of cells in cell culturing systems, the separation of different types of cells from mixed cell cultures, and the implantation of peptide-coated prosthetic devices. These uses are explained in greater detail in Example 6 below. Furthermore, as explained in greater detail in Example 6 below, the haptotactic peptides of the present invention can also be used as tools for biological analysis and for further research and development.

These contemplated compositions, composites and uses of the peptides of the present invention are outlined in the examples below and are intended as illustrations only and are not meant to be limiting in any way.

DETAILED DESCRIPTION OF THE PRESENT INVENTION

The present invention is drawn towards novel peptidic sequences of fibrin. Methods of using these peptidic sequences are also contemplated, including methods for the promotion of wound healing as well as diagnostic methods. These peptidic sequences retain desirable properties exhibited by the entire fibrin molecule, such as cell haptotaxis.

The principles and operation of such peptidic amino acid sequences of fibrin and related sequences according to the present invention may be better understood with reference to the non-limiting illustrative examples below.

The peptides of the present invention (CαE (SEQ ID NO:3), Cβ (SEQ ID NO:1), PreCγ (SEQ ID NO:2)) as well as control peptides (Cα(SEQ ID NO:4) and Cγ (SEQ ID NO:5)) were synthesized and tested in cell culture systems as described below. The experimental procedure is described in the section entitled "Experimental Procedure". The results are given in the section entitled "Results".

Essentially, designated peptides peptide-Cα (SEQ ID NO:4), peptide-Cβ (SEQ ID NO:1), peptide preCγ (SEQ ID NO:2) and peptide-CαE (SEQ ID NO:3) were synthesized and covalently attached to sepharose beads, to form SB-Cα, SB-Cβ (SEQ ID NO:1), SB-preCγ (SEQ ID NO:2) and SB-CαE (SEQ ID NO:3), respectively. Fibrinogen was also covalently attached to sepharose beads, to form SB-Fib. The SB-ligand combination was then incubated with cultured cells. The data are shown in the "Results" section below (Table 3). In summary, SB-Cβ (SEQ ID NO:1) and preCγ (SEQ ID NO:2) appeared to be the most potent for cell binding, showing even greater potency than SB-Fib for all cell lines which bind fibrin(ogen). All tested cell lines bound to SB-Cβ (SEQ ID NO:1) under these conditions, with the exception of OV-1063, keratinocytes and cells derived from a leucocytic lineage. The next most potent peptide/bead combination was SB-CαE (SEQ ID NO:3), as strong binding was observed for SB-CαE (SEQ ID NO:3) for the following cell lines: HF, MF, EC and EMT-6. Weak attachment of SMC cells to SB-CαE (SEQ ID NO:3) was also observed. Variable haptotaxis of SB-Cγ (SEQ ID NO:5) to EC was observed. No cell binding was observed to SB-Cα (SEQ ID NO:4).

Furthermore. FITC-labeled peptides Cβ (SEQ ID NO:1) and CαE (SEQ ID NO:3) were clearly able to bind to the cell membrane, and after a prolonged exposure, accumulated in the cytoplasm, and migrated to the perinuclear area and granular bodies.

Experimental Procedures

Preparation of Peptides

Peptidic analogues of the carboxy termini fibrinogen were synthesized according to standard techniques (Synthetic Peptide Corp., Dublin, Calif. USA). The amino acid sequences of these analogues are given in Table 1 above. Each peptide was labeled with a fluorescent label which was either fluorescein or EACA (epsilon amino caproic acid). The labeling was performed according to well known methods in the art, for example during the synthesis of the peptide itself.

Preparation of Sepharose Beads with Bound Peptides or Proteins.

Peptides or fibrinogen were covalently bound to CNBr activated sepharose beads (SB) (Pharmacia, Piscataway, N.J.) using techniques previously used to bind albumin, fibrinogen and thrombin. Briefly, CNBr-activated sepharose 4B (Pharmacia) was washed with 1N HCl, and suspended in the coupling buffer (pH 8.3), following the protocol supplied by the manufacturer. The peptides were dialyzed against the coupling buffer to remove Tris. Peptides (1 mg) were not highly water soluble. The peptides were dissolved in 1 mL 70% ethanol or dimethylformamide, and were then mixed into the coupling buffer containing 1 mL CNBr-activated sepharose. The suspension was gently agitated overnight, then centrifuged 500×g to pack the beads. This procedure covalently binds more than 95% of proteins or peptides including fibrinogen or peptides—CαE (SEQ ID NO:3), Cβ (SEQ ID NO:1) and preCγ (SEQ ID NO:2) to the beads determined by $Abs_{280}$ readings of the solutions.

Concentrations of peptides bound to SB were: peptide Cα (SEQ ID NO:4) was 7 mg/mL; peptide Cβ (SEQ ID NO:1) was 5.2 mg/mL; peptide CαE (SEQ ID NO:3) was 6.0 mg/mL; peptide preCγ (SEQ ID NO:2) was 5.5 mg/mL. The coated beads were washed with Tris-saline buffer and stored at 4° C. with 0.1% azide. Before use, the beads were washed 3 times in sterile saline to remove all traces of azide.

After incubation with cells, samples of beads were prepared for scanning electron microscopy (SEM) by fixing with 4% glutaraldehyde, critical point dried, and coated with osmium tetroxide, sputter coated with Au/Pd and then examined with a Hitachi S-530 Scanning Microscope.

Preparation of Cell Cultures.

All cell cultures were prepared as previously described. Normal human skin fibroblasts (HF) were isolated from skin biopsies of young human subjects. The dermal layer of skin was chopped and digested for 1 hour by 0.25% trypsin/versen. The isolated cells were washed and plated on plastic Petri dishes with DMEM supplemented by 10% fetal calf serum (FCS), antibiotics, and glutamine. The plates were washed after 10 hrs to select for the better attached fibroblasts. At the 3–4 passage, the cells consisted of homogeneous populations of fibroblasts, as judged by microscopy. Immunohistology with monoclonal anti-human-fibroblast-surface proteins confirm that this procedure yields homogeneous fibroblast culture (Ronnov-Jessen L, Celis J E, Van-Deurs B, Petersen O W: "A fibroblast-associated antigen: characterization in fibroblasts and immunoreactivity in smooth muscle differentiated stromal cells", *J. Histochem. Cytochem.* 40: 475–486 (1992)). Normal murine fibroblasts (MF) were isolated from the skin of 2–3 days old neonate C3H mice by 3 step digestion, each for 2 hrs, with trypsin/versen. The use of neonate mice with low cross linking of collagen served to enhance the high yield of cells during the proteolytic digestion. The details of the rest of the protocol are similar to those used for the isolation and growth of HF. These cells could be grown for at least 12–14 passages before any decrease of the rate of proliferation occurred. Cells were used from the fourth passage to the tenth passage.

Porcine smooth muscle cells (SMC) were isolated from thoracic aortas of young animals and kept in culture with twice weekly medium change and splitting once in 1–2 week. Cells of up to 10 passages were used. The purity of the SMC culture was verified by immunohistology with monoclonal anti muscle-specific-actin HHF-35 (Bar-Shavit R, Benezra M, Eldor A, Hv-Am E, Fenton J W, Wilner G D & Vlodavsky I: "Thrombin immobilized to extracellular matrix is a potent mitogen for vascular smooth muscle cells: nonenzymatic mode of action", *Cell Regul.* 1: 453–463, 1990). Other cell lines were obtained from different sources and cultured in their standard conditions as described in the following references: murine fibroblast line (3T3) and normal human keratinocytes (Ben-Bassat H, Eldad A, Chaouat M, Livoff A, Ron N, Neeman Z, and Wexler M R: "Structural and functional evaluation of modifications in the composite skin graft: cryopreserved dermis and cultured keratinocytes". *Plastic & reconstructive Surgery* 89: 510–520 (1992)); murine mast cells (MC-9) (Razin E, and Marx G. "Thrombin-induced degranulation of cultured bone marrow-derived mast cells", *J. Immunol.* 133: 3282–3285 (1984)); normal bovine aortic endothelial cells (BAEC) (Vlodavsky I, Greenburg G, Johnson L K and Gospodarowicz D: "Vascular endothelial cells maintained in the absence of fibroblast growth factor undergo structural and functional alterations that are incompatible with their in vivo differentiated properties", *J. Cell Biol.* 83:468–486, 1979); porcine smooth muscle cells, isolated and cultured as previously described (Bar-Shavit R, Benezra M, Eldor A, Hy-Am E, Fenton J W, Wilner G D & Vlodavsky I: "Thrombin immobilized to extracellular matrix is a potent mitogen for vascular smooth muscle cells: nonenzymatic mode of action", *Cell Regul.* 1: 453–463, 1990); murine leukemic cells (P-388) (Ramu A, Ramu N.& Gorodestsky R. "Reduced oubain resistant potassium entry as a possible mechanism of multidrug-resistance in p388 cells", *Biochem. Parmacol.*, 42: 1699–1704 (1992)); human ovarian carcinoma cells (OV-1063) were isolated from a primary tumor and then maintained as previously described (Horowitz A T, Treves A J, Voss R, Okon E, Fuks Z, Davidson L, and Biran S., "A new human carcinoma cell line: establishment and analysis of tumor associated markers", *Oncology* 42: 332–337 (1985)); murine mammary adenocarcinoma cells (EMT-6) were grown under the standard conditions (Rockwell S., "Cytotoxic and radiosensitizing effects of hypoxic cell sensitizers on EMT6 mouse mammary tumor cells in vivo and in vitro", *Br J Cancer* 37: 212–215 (1978)); and the murine macrophage-like cells (J774.2) (Ringel R, Roy S N, and Horwitz S B., "A phosphoglycoprotein associated with taxol resistance in 1774.2 cells", *Cancer Res.* 45: 3856–3863 (1985)).

All culture medium components were purchased from Biological Industries (Beit-HaEmek, Israel) and fetal calf serum was supplied by GIBCO (Grand Island, New York, N.Y., USA). The cell cultures were maintained at 37° C. in a water-jacketed $CO_2$ incubators, and were harvested by trypsin/versen solution with 1–2 passages per week in a split ratio of 1:10 for fast proliferating transformed cells and 1:4 for normal cell types.

Assays for Cell Proliferation

Cell proliferation was evaluated by measuring cell density as a function of time by two different colorimetric assays. The MTS colorimetric assay (CellTitre 96 Aqueous Assay by Promega) is based on dehydrogenase conversion of MTS (methyl tetrazolium salt) by viable cells to colored tetrazolium salt (Ge M., Tang, G., Ryan, T. J. and Malik, A. B., "Fibrinogen degradation product fragment D induces endothelial cell detachment by activation of cell-mediated fibrinolysis", *J. Clin. Inves.*, 90:2508–2516 (1992)); the methylene blue (MB) assay is based on the staining of monolayer cells after their fixation, and reading the absorbence of the absorbed dye.

The MTS assay for viable cells was performed as follows: 30 µL of freshly prepared MTS/PMS were added to each well: following 2 hrs incubation at 37° C., the plates were placed on a computer driven microplate reader (Anthos HT-II, Salzburg, Austria), programmed to shake the plate for 1 minute before reading the optical density (OD) of the dye at 490 nm. The measurements were repeated following 4 and 6 hours of incubation.

% Haptotaxis Activity Assay for Monitoring Cell Adhesion to Peptides Bound to Sepharose Beads (SB).

The migratory/adhesion response of cells to proteins (such as fibrinogen) or peptides covalently bound to SB was measured as follows. Cells were grown in 6 or 12 well plates to near confluence or in suspension until they covered about ½ to ⅔ of the plate surface. At that point, about 20–50 mL of a suspension containing 50% v/v SB coated with the test protein or peptide were added to the plate and dispersed by gentle shaking for 1 min. The plate was then returned to the incubator and examined at different times by inverted phase microscopy.

The SB (naked or ligand bound) sedimented onto the nearly confluent cell layer and occasionally made physical contact with cell membranes on the plate (ascribed to Brownian motion or micro-convection currents). In a positively responding system, this resulted in the tethering of SB to the cell layer, which could be detected by visual inspection at different time points. Typically, 300 beads (but not less then 200) were counted in each well and the ratio of SB bound to the cells relative to total number SB could be calculated (SB bound/SB total). Counting the percentage of SB attached to the cell surface at different time intervals provided a quantitative assay of the kinetics of the attachment of coated beads to cells. Negative control with uncoated SB or positive controls with SB-fibrinogen were employed with at least 3 wells measured for each. The statistical error was calculated from the square root of the total counts.

After incubation with cells, samples of beads were prepared for scanning electron microscopy (SEM) by fixing with 4% glutaraldehyde, critical point dried and coated with osmium tetroxide, sputter coated with Au/Pd and then examined with an Hitachi S-5390 Scanning Microscope.

Electron Microscopy

Samples of the cells with attached sepharose beads were fixed as described previously, and were then examined with a Hitachi S-530 Scanning Microscope (SEM).

Fluorescence Microscopy

The cells examined were grown in 6-well plates on cover slips to reach near confluence. At the time of examination, the cover slips were inverted and put on a microscope slide supported by 2 thin spacers so that a thin gap (~2 min) was left between the cells on the coverslip and the slide. This was filled with culture medium. To follow the uptake, 10 µg/mL FITC-labeled peptide Cβ (SEQ ID NO:1) or CαE (SEQ ID NO:3) was added into the culture medium in the gap. At different time points, medium was replaced with fresh medium and the fluorescence was viewed and photographed, using an Olympus fluorescent microscope system.

Cell Migration (Chemotaxis) Assay

Chemotaxis was evaluated using 48-well plastic Microtaxis micro-Boyden chambers. Polycarbonate filters with pore size of 8 µM were coated with fibronectin for 2 hours at 37° C. Conditioned medium from 3T3 cells served as a positive control. Test solution (26 µl) containing the tested peptides or protein or medium with no additions that served as control were placed in the lower chamber, covered with the filter. 50 µl cell suspension was introduced to the upper chamber of each well. The number of cells/well varied in the range of 5,000–10,000 in different experiments. The device loaded with cells was incubated at 37° C. for 4–5 hours. The filter was then removed and the non-migrating cells on its upper part were carefully wiped off with a damp cotton swab. The filter was fixed in methanol and stained with Accustain (modified Wright stain solution Sigma Diagnostics. St. Lois, Mo.). Cells that crossed or were retained within the filter were counted microscopically at low magnification so that the viewing field corresponded to the whole area of each well. Each experimental variant was performed in duplicated or triplicates and the data from, three successful experiments were normalized to the values of the positive control and averaged.

Results

EXAMPLE 1

Haptotactic Effect of the Peptides

The peptides of the present invention were synthesized and tested in cell culture systems as described above. Essentially, peptides were covalently attached to sepharose beads to form SB-Cα (SEQ ID NO:4), SB-Cβ (SEQ ID NO:1), SB-PreCγ (SEQ ID NO:2), SB-Cγ (SEQ ID NO:5) and SB-CαE (SEQ ID NO:3), respectively, as was fibrinogen to form SB-Fib. The SB-peptide combination was then incubated with cultured cells. Under these conditions all tested cell lines bound to SB-Cβ (SEQ ID NO:1) and its homologues SB-PreCγ (SEQ ID NO:2) and SB-CαE (SEQ ID NO:3), with the exception of OV-1063, keratinocytes and cells derived from a leucocytic lineage. The haptotactic potency of the peptides is summarized in Table 3 with the percentage of SB-Fib/peptide attached to cells (by day 4) given in columns 2–5 of Table 3.

Figure 1:
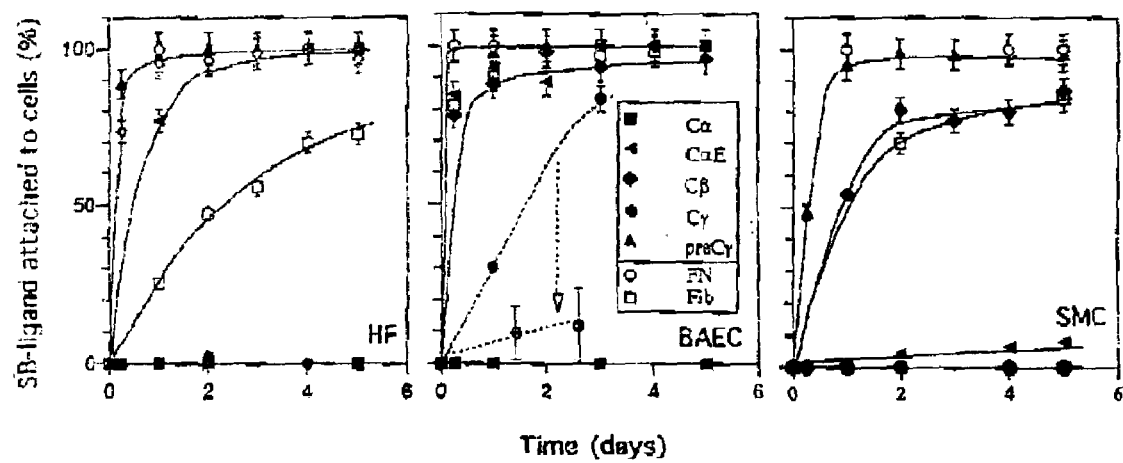
FIG. 1 shows the haptotactic responses of cells to sepharose beads (SB) coated with active C-terminal fibrinopeptides (either Cβ (SEQ ID NO: 1), preCγ (SEQ ID NO:2) and CαE (SEQ ID NO:3)) in comparison with positive controls fibrinogen (Fib) or fibronectin (FN) and in contrary to non-active Cα peptide (SEQ ID NO:4) and the minor negligible activity of the Cγ peptide (SEQ ID NO:5). The ligands covalently-bound to SB were added to near confluent cell culture of SMC, HF and BAEC in 12-well plates. The rate of attachment was monitored visually by counting the % of attached SB over time. The Cα (SEQ ID NO:4) was inactive, whereas Cβ (SEQ ID NO:1), preCγ (SEQ ID NO:2) and to a lesser degree CαE (SEQ ID NO:3) were highly haptotactic, with response kinetics equivalent to fibrinogen and somewhat less than with fibronectin.

Three homologues of fibrinogen carboxy termini were active in attracting and binding to most of the mesenchymal cell lines tested, as shown FIG. 1. For example, SB-Cβ (SEQ ID NO:1) bound to 5 out of 7 cell lines with higher efficacy than SB-Fib. Sepharose beads coated with peptide CαE (SEQ ID NO:3) (SB-CαE) bound to 5 out of 7 tested cell lines. Sepharose beads coated with PreCγ (SEQ ID NO:2) (SB-PreCγ) bound to HF, SMC and EC cells, whereas Sepharose beads coated with peptide Cγ (SEQ ID NO:5) bound variably only to EC, and Sepharose beads coated with peptide Cα (SEQ ID NO:4) (SB-Cα) bound to none.

TABLE 3

% Binding of peptide-coated SB to normal cultured cells.

| Cell Line | Control -Fib | SB-Ligand | | | | |
|---|---|---|---|---|---|---|
| | | -Cα (SEQ ID NO: 4) | -Cβ (SEQ ID NO: 1) | Pre-Cγ (SEQ ID NO: 2) | -Cγ (SEQ ID NO: 5) | -CαE (SEQ ID NO: 3) |
| HF | 71 | 0 | 100 | 100 | 2 | 52 |
| MF | 81 | 0 | 89 | ND | 0 | 61 |
| SMC | 74 | 0 | 100 | 98 | 1 | 8 |
| EC | 70 | 0 | 94 | 100 | 2 to 93* | 43 |
| EMT-6 | | 1 | 99 | ND | 2 | 64 |
| Keratinocyte | 5 | 0 | 0 | ND | ND | 0 |
| OV-1063 | | 0 | 4 | ND | 0 | 0 |

*Response varied with different cell batches.
**ND - Not determined

FIG. 1 shows the kinetics of the haptotactic effect (attachment) of the SB-peptides of the present invention for various cell types.

Thus, these tests demonstrate the haptotactic activity of 3 short (19–21 mer) peptides, homologues of fibrinogen carboxy terminal regions. FIG. 2 also shows the ability of these peptides to render otherwise inactive material, such as Sepharose into a haptotactic material, and illustrates the utility of SB coated with these peptides.

EXAMPLE 2

Effect of the Haptotactic Peptides on Cell Proliferation

Figure 7:
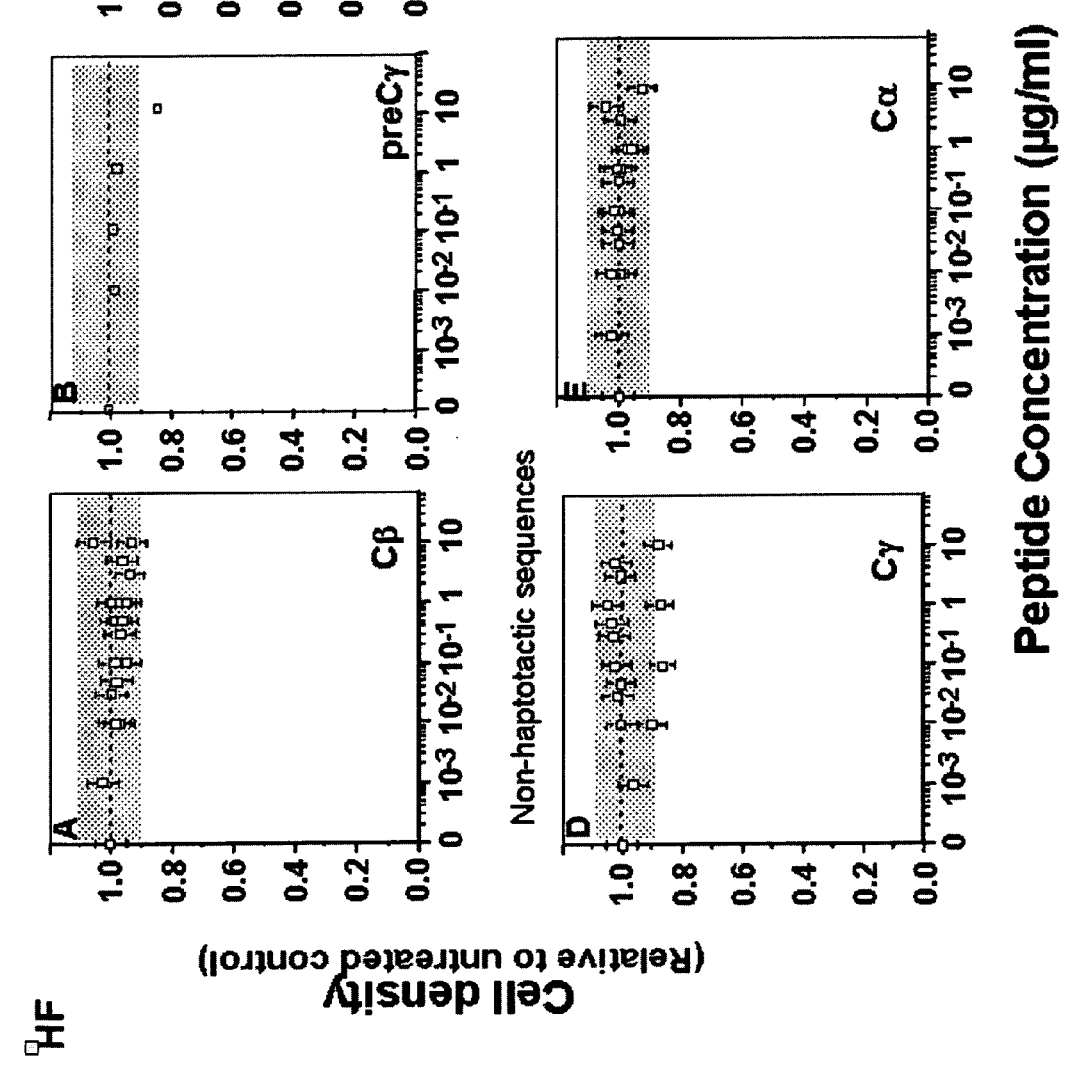
FIG. 7 shows the lack or proliferative response of HF exposed to the active Cβ (SEQ ID NO:1) panel C, CαE (SEQ ID NO:3) panel B, and pre Cγ (SEQ ID NO:2) panel E, peptides versus the less active Cα (SEQ ID NO:4) panel A and Cγ (SEQ ID NO:5) panel D peptides that served as negative controls. The peptides were tested in a concentration of 0.4 nM–4 μM in 96 well plates with the MTS proliferation assay. Clearly none of these peptides stimulated or inhibited proliferation at any concentration.

Peptides (Cα (SEQ ID NO:4), Cβ (SEQ ID NO:1), PreCγ (SEQ ID NO:2) and CαE (SEQ ID NO:3)), up to 1 µg/mL or 100 µg/mL fibrinogen or thrombin (final concentrations) were added to the culture medium and cell numbers were assayed by day 3 using the MTS assay. The change in cell number was compared with that observed versus saline control. Of the 5 peptides tested at dosages up to 10 µg/l mL (approximately equimolar to 1 µg/mL fibrinogen), none of the peptides exerted significant effect on cell proliferation (FIG. 7).

EXAMPLE 3

Uptake of FITC-Cβ and FITC-CαE by Cells by Fluorescence Microscopy

Figure 3:
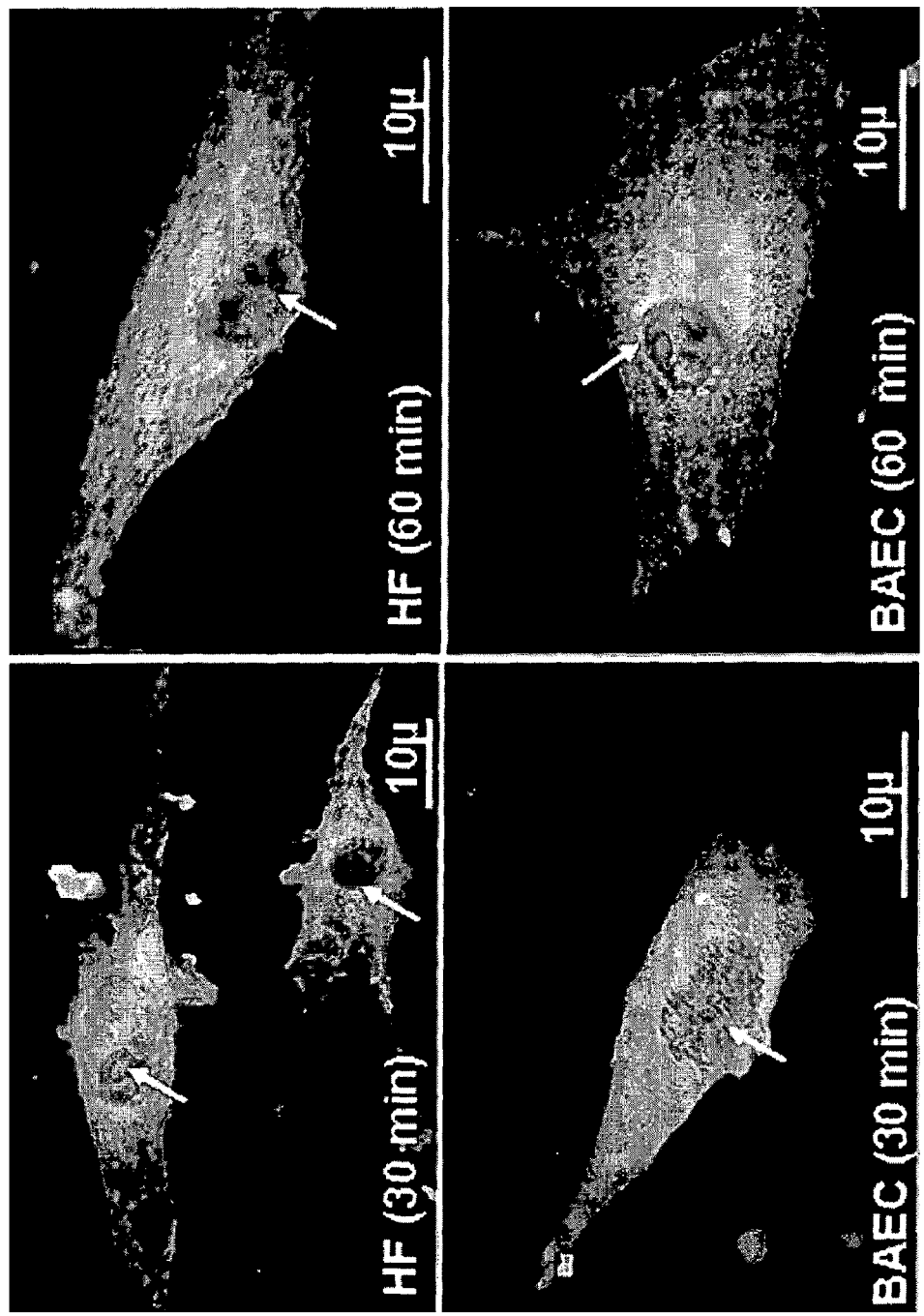
FIG. 3 shows binding and internalization of dissolved Cβ$^{FITC}$ (SEQ ID NO:1) and CαE$^{FITC}$ (SEQ ID NO:3) to BAEC and HF as viewed by fluorescent microscopy (objective x40). HF (A and B) and BAEC (C and D) were incubated with 100 μg/ml of CαE$^{FITC}$ (SEQ ID NO:3) for 30 min (A and C respectively) and 60 min (C and D respectively) and Cβ$^{FITC}$ (SEQ ID NO:1) (C and D respectively). The arrow points to the cell nuclei. Confocal microscopy showed the FITC peptides distributed over the cell surface and in the cytoplasm with little penetration into the nucleus. Cells initially accumulated tagged peptides in the cell membrane and after a prolonged exposure distributed within the cytoplasm to the perinuclear area and into granular bodies.

Exposure of cultured human fibroblast cells to a solution of 10 µM peptide FITC-CαE (SEQ ID NO:3) resulted in uptake by human fibroblasts as shown by fluoro-microscopy (FIG. 3). Accumulation of the FITC-peptide in the cytoplasm and around the nucleus was clearly observed. Exposure of cultured HF, EC and SMC cells to solutions of 10 micromolar peptide FITC-Cβ (SEQ ID NO:1) resulted in significant uptake similar to that seen with peptide-CαE (SEQ ID NO:3). After a short exposure of the cells to 10 μM of peptide FITC-Cβ (SEQ ID NO:1), the FITC-peptide was observed to bind to the cell membrane. After a longer exposure of more than 1 hour or with fixed cells accumulation of the FITC-peptide in the cytoplasm and around the nucleus was clearly observed (data not shown). In most cases, the fluorescence became concentrated in discrete cytoplasmic vesicles.

EXAMPLE 4

FACS Analysis and Uptake of FITC-Labeled Peptides-Cβ (SEQ ID NO:1) and CαE (SEQ ID NO:3)

EC and HF cell monolayers were washed and then incubated with trypsin-versene. Cells were then washed with growth medium and resuspended in medium with 0.1% albumin. FITC-labeled peptide-Cβ (SEQ ID NO:1) was incubated with $5 \times 10^5$ EC cells (10 μg/ml or 100 μg/ml) or with $2.5 \times 10^5$ HF cells (110 μg/ml) in medium with 0.1% albumin. FITC-labeled peptide-CαE (SEQ ID NO:3) and Cα (SEQ ID NO:4) (10 μg/ml) was incubated with $5 \times 10^5$ EC cells in medium with 0.1% albumin. Cells were then washed with PBS and 1% albumin. Cells were resuspended in PBS and 1% albumin and then filtered through a mesh for FACS analysis, in which the FITC fluorescence was measured for each cell.

Figure 4:
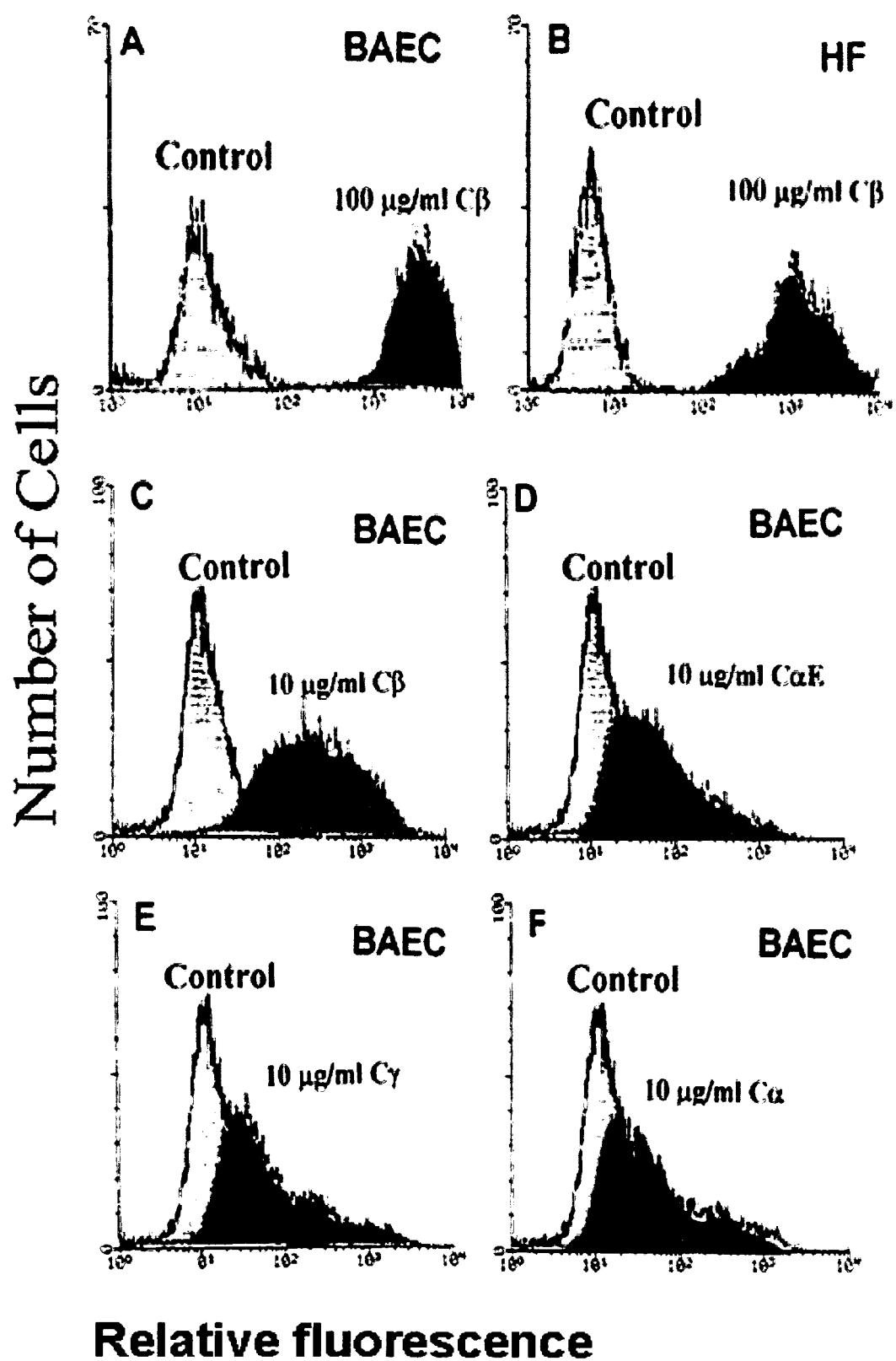
FIG. 4 shows FACS analysis of FITC-labeled fibrinopeptides—Cβ (SEQ ID NO:1) (FIGS. 4A–4C), CαE (SEQ ID NO:3) (FIG. 4D), Cγ (SEQ ID NO:5) (FIG. 4E) and Cα (SEQ ID NO:4) (FIG. 4F). Control represents the autofluorescence of cells not exposed to FITC-peptides. While Cβ (SEQ ID NO:1) and to a lesser degree CαE (SEQ ID NO:3) clearly bound to cells, Cα (SEQ ID NO:4) served as a negative control and did not bind to them.

FIG. 4 shows FACS analysis of the binding of soluble FITC-labeled peptides—Cβ (SEQ ID NO:1) (FIGS. 4A–4C), CαE (SEQ ID NO:3) (FIG. 4D), Cγ (SEQ ID NO:5) (FIG. 4E) and Cα (SEQ ID NO:4) (FIG. 4F). The x-axis shows fluorescence in arbitrary units and the y-axis shows number of cells. The control is without FITC-labeled peptide (background fluorescence). Similar binding was seen to EC and HF cells with 100 μg/ml FITC-labeled peptide-Cβ (SEQ ID NO:1). FITC-labeled peptide-CαE (SEQ ID NO:3) also was taken up by cells. By contrast, FITC-labeled peptide Cα (SEQ ID NO:4) and Cγ (SEQ ID NO:5) bound only slightly (non-specifically) to cells. It is expected that the haptotactic preCγ (SEQ ID NO:2) would act in a similar way to Cβ (SEQ ID NO:1) (results not shown).

Figure 5:
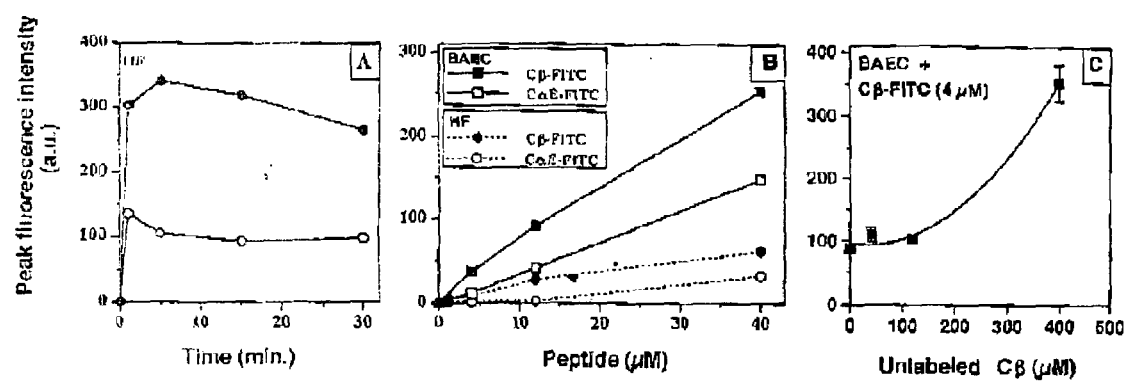
FIGS. 5A, 5B and 5C show the concentration dependence of haptotactic peptide uptake to cells as determined by FACS analysis.

Kinetics FACS experiments with FITC-peptides showed that binding of Cβ (SEQ ID NO:1) and its CαE (SEQ ID NO:3) analogue by cells such as HF or BAEC is fast and can reach a maximum within 2–5 minutes (FIG. 5A). Similar kinetics binding of Cβ and CαE was observed for both BAEC and HF. The affinity of cells to peptide was higher in BAEC than HF and in both cell types, the uptake of Cβ (SEQ ID NO:1) was higher than that of CαE (SEQ ID NO:3). In competition experiments, cells were incubated with various concentrations of unlabeled Cβ (SEQ ID NO:1) for 15 mins, an aliquot of $Cβ^{FITC}$ (4 mM) was added and the sample was subjected to FACS analysis. Paradoxically, rather than competing with $Cβ^{FITC}$, elevated concentrations of cold peptide increased the level of total Cβ (SEQ ID NO:1) uptake by cells (FIG. 5). The $Cβ^{FITC}$ (SEQ ID NO:1) uptake experiments best fitted a linear-quadratic curve-fit. Consequently, an attempt to plot a Scatchard curve from the data could not yield a $K_D$ associated with saturation of binding. Rather, the data indicate cooperative binding kinetics, possibly associated with receptor clustering or peptide endocytosis.

EXAMPLE 5

Chemotactic Effect of Peptides on Migration of Bovine Endothelial Cells

Figure 6:
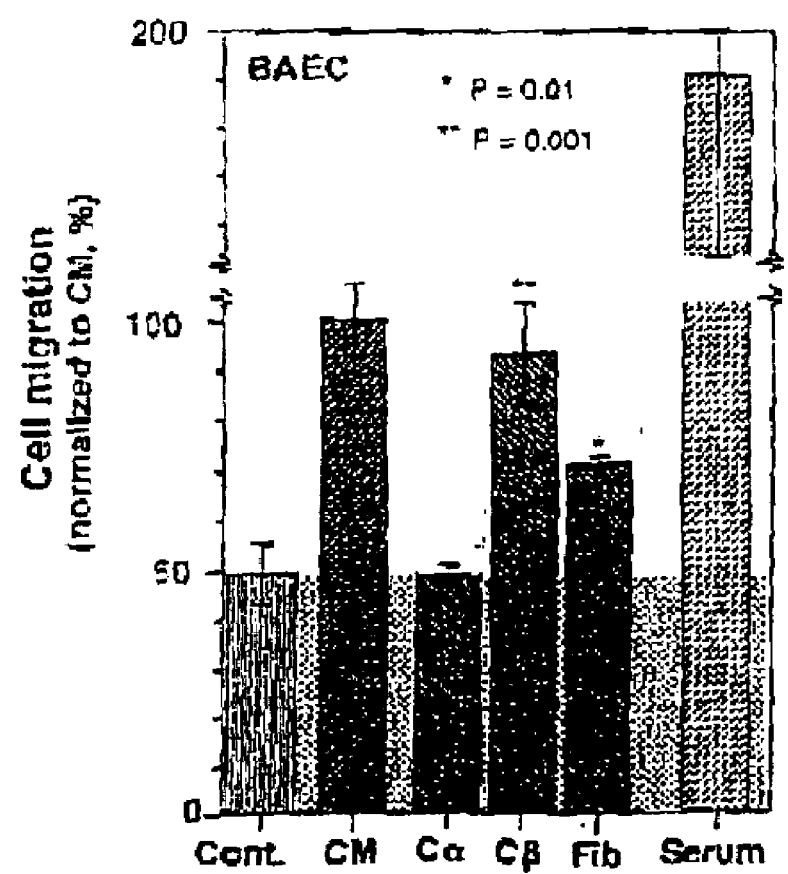
FIG. 6 shows the chemotaxis of BAEC to Cβ (SEQ ID NO:1) gradient in multi-chamber micro-Boyden assay. Similar results were obtained with HF. Cells that transversed through the membrane were stained and counted, Cα (SEQ ID NO:4) elicited no response relative to negative control with no additions, whereas conditioned medium (CM) served as positive chemotactic control that induced 100% migration. The values and errors represent over 5 repeated experiments for each of the agents.

The chemotactic response of BAEC to a soluble gradient of Cβ (SEQ ID NO:1), the most haptotactic of the peptides studied was as follows. The results can be seen in FIG. 6. At concentrations of Up to 40 μg/ml Cβ (SEQ ID NO:1) induced highly significant chemotaxis, similar to that induced by conditioned medium (CM), which served as a positive control (100% chemotaxis). This response was significantly higher than that of fibrinogen and 3 times higher than the results obtained with the negative control of 1% BSA serum-free medium. A similar, though more moderate, chemotaxis response to Cβ (SEQ ID NO:1) was obtained with HF. At concentrations of up to 40 μM PreCγ (SEQ ID NO:2) also induced significant chemotaxis. The results suggest that the cellular haptotaxis is also associated with chemotactic properties.

EXAMPLE 6

Structured Cell Systems Using the Haptotactic Peptides of the Present Invention

The peptides of the present invention could be used as part of structured cell systems, for example as for tissue engineering. The cell system of the present invention includes at least one type of cell bound to at least one haptotactic peptide of the present invention. Suitable types of cells include any cells which are capable of binding to at least one peptide of the present invention. Examples of such cells may include, but are not limited to, fibroblasts, endothelial cells, chondrocytes, neuroblastoma cells, melanoma cells, kidney cells, liver cells, pancreatic cells, thyroid cells, glial cells, smooth muscle cells, mouse mammary carcinoma cells, bone or cartilage forming cells, and combinations thereof.

The cell system of the present invention could also be used to culture cells as part of a cell culture system. At least one type of cell would be allowed to bind to the peptide of the present invention. The cells would then be grown in a culture medium under suitable conditions for cell culture. The advantage of such a cell culture system is that the peptide of the present invention could be attached to a suitable structure, such as a sepharose bead or glass or collagen or any other geometrically and biologically suitable structure, thereby rendering it attractive to select cell types. Hereinafter, the term "structure" includes but is not limited to the term "matrix".

The cells would then attach and grow on that structure, rather than on a conventional Petri dish. Therefore, when ready for implantation or for moving to another cell growth system, the cell-coated structure would be removed from the culture medium without trauma to the cells. By contrast, conventional methods for removing cells from culture medium often require trypsinization, which may damage certain receptors on the cells and otherwise cause trauma to the cells. The ability to transfer cells from one environment to another by moving the structure or matrix on which cells are attached, also enables the cells to be re-seeded into fresh culture medium with minimal damage to the cells.

Such a cell culture system which incorporates the peptides of the present invention could also be used to culture the cells at a higher density than conventional cell Cultures. Such high density cell cultures are particularly useful for the production of recombinant proteins and for other types of cell culture products. The cell culture system of the present invention could be used to transfect cells with various vectors, viruses, nucleic acids and the like, in order to facilitate the production of the cell culture products or to genetically modify the cells themselves.

The peptides of the present invention could also be used to separate cells which are capable of binding to one or more of these peptides from those cells which are not capable of binding to such peptide(s). For example, a peptide of the present invention could be attached to a matrix or structure as described previously. This structure or matrix could then be incubated with a mixture of cells in solution, under suitable conditions to enable binding of those cells which are capable of binding to the peptide. The structure or matrix could then be removed, and with it the bound cells. Cells which are not capable of binding to the peptide, whether because these cells are of a type which does not bind or because the cells have been damaged in some way, would remain behind. As an additional example, a peptide of the present invention could be attached to a substantially immobile support (such as the surface of a prosthetic device), and the solution of cells could be placed in contact with it. Those cells which are capable of binding to the peptide would remain bound to the support, while the other cells would be removed. Thus, the peptides of the present invention could be used for separation of cells and for coating the surface of such a device.

Such separation may also prove useful for diagnostic purposes. For example, the presence or absence of a certain type of cell, or of a certain cell function, could be determined by examining whether the cell bound to the peptide. The presence or absence of substantially any cell type which binds to one or more of the peptides of the present invention could be determined in such an assay (such as by fluorescent cell sorter analysis). Examples of cell functions which can be diagnosed include, but are not limited to, the ability to respond to a chemotactic or an attachment signal.

These functions would be assessed by the determination of cell binding to the peptide-coated structure. The determination of cell binding could be performed by the ability to separate the cell from a solution or mixture of different cell types, as described previously.

Alternatively and preferably, the peptide could be labeled with a reporter, such as a fluorescent or radioactive moiety. The reporter would be used to determine if the peptide had bound to any of the cells, thus enabling the presence or absence of the cell type, or of a certain cell function, to be determined.

Examples of suitable fluorescent moieties include, but are not limited to, FITC (fluorescein), rhodamine and Texas red. Examples of suitable radioactive moieties include, but are not limited to, phosphorous 32, iodine 131 and tritium. The reporter could be attached to the peptide during synthesis or alternatively post-synthesis, according to well known methods in the art.

The haptotactic peptides of the present invention are also contemplated as being useful for the formation of a therapeutic structure of cells. Examples of the therapeutic structure include, but are not limited to, a gel, a prosthetic device, and a collagen sheet. At least one peptide of the present invention would be attached to the therapeutic structure, for example by a covalent bond formed with a chemical cross-linking reagent as is well known in the art, or with fibrin glue. The cells would then be allowed to attach to the peptide on the therapeutic structure, for example through cell culture or by the separation methods described above. The choice of cells will depend upon the type of tissue being contacted and the desired therapeutic structure, and could potentially include any cell type which is capable of binding to at least one peptide of the present invention.

EXAMPLE 7

Methods for Treatment with the Haptotactic Peptides of the Present Invention

The haptotactic peptides of the present invention are contemplated as being useful for treatment of a subject with a disease condition in which the condition can be ameliorated or cured, at least in part, through cell chemotaxis or proliferation, or by transplantation of cells. Examples of such a condition include, but are not limited to, the presence of a wound and diseases characterized by an absence of a cell product. The term "wound" includes any disruption of the normal integrity of an organ of the subject. Examples of such an organ include, but are not limited to, the skin, the abdominal cavity, the intestine, the heart, the lungs, any blood vessel, any bone, the pancreas, the liver, a kidney, the reproductive organs or the stomach.

The wound may be present as the result of a surgical intervention or as the result of a non-surgical intervention. The surgical intervention could be either planned or as the result of a medical emergency. The non-surgical intervention could be a burn, an ulcer, a laceration or any type of accidental injury or trauma.

Methods of treatment with the haptotactic peptides of the present invention for surgical intervention could include placing one or more of the peptides at the site of the surgical intervention, in order to increase the efficiency of the wound healing process. The one or more peptides could be placed at the site of the surgical intervention before surgery, particularly for emergency surgery, during surgery or after surgery. The one or more peptides could be included in a therapeutic composition, as described in Example 8 below.

Methods of treatment of non-surgical interventions would include placing one or more of the peptides at the site of the non-surgical intervention, in order to increase the efficiency of the wound healing process. The one or more peptides could also be included in a therapeutic composition, as described in Example 8 below.

The one or more peptides of the present invention could be placed at the site of the surgical or non-surgical intervention once, or repeatedly, depending upon the type and gravity of the wound which was sustained. The concentration and rate of treatment, if repeated, could easily be determined by one of ordinary skill in the art.

Examples of diseases characterized by an absence of a cell product include, but are not limited to, diabetes mellitus, hemophilia A (factor VIII deficiency), hemophilia B (factor IX) deficiency and Parkinson's disease. These diseases could be ameliorated or cured by introducing cells which produce the necessary cell metabolite or product into the subject. These cells could be prepared by introduction of a vector containing the nucleic acid sequence coding for a protein or peptide, for example, as is well known in the art. The peptide or protein could itself be the desired cell product, such as insulin. Alternatively and preferably, the protein could cause the cell to produce the desired cell product, for example through an enzymatic reaction or reactions. In any case, the cell would then be able to produce the desired cell product after such preparation.

Once prepared, the cells would be attached to a haptotactic peptide of the present invention, which would in turn be incorporated within a suitable cell structure as described in Example 6. The cell structure would be administered to the subject and would then produce the necessary cell metabolite or product. The advantage of such a cell structure according to the present invention is that the cells would remain substantially localized, although the cell products could be enabled to enter the bloodstream if desired. Thus, by using the haptotactic peptide of the present invention, the cell structure could be used to treat the disease condition with the necessary cell metabolites or products.

EXAMPLE 8

Suitable Formulations for Administration of the Haptotactic Peptides

The haptotactic peptides of the present invention can be administered to a subject in a number of ways, which are well known in the art. Hereinafter, the term "subject" refers to the human or lower animal to whom the peptide was administered. For example, administration may be done topically (including opthalmically, vaginally, rectally, intranasally), orally, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

The haptotactic peptides of the present invention may be placed on the would bed as part of a composition for wound treatment. The composition for wound treatment can include a suitable pharmaceutically acceptable carrier. For example, the haptotactic peptide could be incorporated into lasered or heated albumin to accelerate wound healing, minimize scarring, accelerate the rate of deposition of new extracellular matrix and augment an angiogenesis.

As another example, a polymer could be made of subunits of at least one of the peptides of the present invention, such that a plurality of these peptides would be linked to form the peptide polymer. The peptides could be linked with a chemical cross-linking moiety, for example. More than one of the peptides of the present invention could be used to form the polymer. Alternatively, at least one of the peptides of the present invention could be attached to a biologically acceptable synthetic polymer, again through a suitable cross-linking moiety, to form a co-polymer. In either case, the resultant peptide polymer or co-polymer could be used to fabricate microparticles which could either be included in a composition according to the present invention, or else could be used form cell structures as described in Example 6 above.

The composition for wound treatment can also include at least one bioactive agent. Suitable bioactive agents include, but are not limited to, drugs, neurologics, vitamins, vitamin derivatives, growth factors, glucocorticosteroids, steroids, antibiotics, antibacterial compounds including bacteriocidal and bacteriostatic compounds, antiparasitic compounds, tumoricidal compounds, tumoristatic compounds, toxins, enzymes, enzyme inhibitors, proteins, peptides, minerals, neurotransmitters, lipoproteins, glycoproteins, immunomodulators, immunoglobulins and fragments thereof, fatty acid derivatives, polysaccharides, cell receptor binding molecules, anti-inflammatories, anti-glaucomic compounds, mydriatic compounds, anesthetics, nucleic acids, polynucleotides and the like.

The therapeutic composition could also include at least one-type of cell in a structured format, as described in Example 6 above. For example, the previously described sheet structure for cell culture could be placed on the wound in order to both protect the wound during the healing process, and to promote the wound healing process itself. The structure could also be the previously described haptotactic peptide-containing gel, which would be placed on the wound for transplanting the cells onto the site of the wound, and would then be able to promote the wound healing process. Other examples of such structured cell systems could also be used as part of the therapeutic composition of the present invention for wound healing. When used for wound healing, suitable cell types include, but are not limited to, fibroblasts, smooth muscle cells, endothelial cells, chondrocytes, bone or cartilage forming cells, and combinations thereof.

Combinations of any two or more of these different components of therapeutic compositions are also possible as therapeutic Compositions of the present invention.

Dosing is dependent on the severity of the symptoms and on the responsiveness of the subject to the peptide or fragments of the present invention. Persons of ordinary skill in the art can easily determine optimum dosages, dosing methodologies and repetition rates.

EXAMPLE 9

Analysis Performed with the Haptotactic Peptides of the Present Invention

The peptides of the present invention are also contemplated as tools for performing analysis of other systems, and for further research and development. For example, the haptotactic peptides could be used to identify and isolate cell receptors. As described previously, the peptide could be labeled with a reporter, such as a fluorescent or radioactive moiety. The reporter would be used to determine if the peptide had bound to any of the cells, thus enabling the presence or absence of the cell type, or of a certain cell function, to be determined.

Examples of suitable fluorescent moieties include, but are not limited to, FITC (fluorescein), rhodamine and Texas red. Examples of suitable radioactive moieties include, but are not limited to, phosphorous 32, iodine 131 tritium. The reporter could be attached to the peptide during synthesis or alternatively post-synthesis, according to well known methods in the art. Thus, the ability of the peptide to bind to a novel receptor or other protein could be determined according to a binding assay.

In addition, the peptides of the present invention could be used to design analogues, such as non-peptide mimetics, of these peptides. Such non-peptide mimetics could be used for therapeutic purposes, for example. Non-peptide compounds are potentially easier to administer, since peptides are preferably administered nasally or parenterally, for example, while non-peptide compounds could potentially be administered orally. Furthermore, particular properties of each peptide could be selected or augmented by designing a specific analogue. Thus, the peptides of the present invention could potentially yield many new and different types of therapeutic medicaments.

While the invention has been described with respect to a limited number of embodiments, it will be appreciated that many variations, modifications and other applications of the invention may be made.

What is claimed is:

1. An isolated peptide consisting of the amino acid sequence as set forth in SEQ ID NO: 1, wherein the peptide has a haptotactic activity.

2. A composition comprising an isolated peptide consisting of the amino acid sequence as set forth in SEQ ID NO:1, wherein the peptide has a haptotactic activity.

3. The composition of claim 2, further comprising a pharmaceutically acceptable carrier.

4. The composition of claim 2, further comprising a biological agent.

* * * * *

UNITED STATES PATENT AND TRADEMARK OFFICE
CERTIFICATE OF CORRECTION

| | |
|---|---|
| PATENT NO. | : 7,122,620 B1 |
| APPLICATION NO. | : 09/487790 |
| DATED | : October 17, 2006 |
| INVENTOR(S) | : Gorodetsky et al. |

It is certified that error appears in the above-identified patent and that said Letters Patent is hereby corrected as shown below:

Title Page:
Item (73) Assignee, please change "Medical Research Services and Development Ltd." to -- Hadasit Medical Research Services Development Company Ltd. --.

Signed and Sealed this

Twentieth Day of May, 2008

JON W. DUDAS
*Director of the United States Patent and Trademark Office*